(12) United States Patent
Jagadale et al.

(10) Patent No.: US 11,957,658 B2
(45) Date of Patent: Apr. 16, 2024

(54) CHLORTHALIDONE COMPOSITIONS AND METHODS

(71) Applicant: Nivagen Pharmaceuticals, Inc., Sacramento, CA (US)

(72) Inventors: Govind R. Jagadale, Sacramento, CA (US); Dasaradhi Lakkaraju, Sacramento, CA (US); Bala Tripura Sundari Chodavarapu, Davis, CA (US); Niravkumar Prajapati, Sacramento, CA (US); Anand Shukla, Denver, CO (US); Jay Shukla, Sacramento, CA (US)

(73) Assignee: Nivagen Pharmaceuticals, Inc., Sacramento, CA (US)

( * ) Notice: Subject to any disclaimer, the term of this patent is extended or adjusted under 35 U.S.C. 154(b) by 48 days.

(21) Appl. No.: 17/331,011

(22) Filed: May 26, 2021

(65) Prior Publication Data

US 2021/0369673 A1 Dec. 2, 2021

Related U.S. Application Data

(60) Provisional application No. 63/032,434, filed on May 29, 2020.

(51) Int. Cl.
| | | |
|---|---|---|
| *A61K 31/4035* | (2006.01) | |
| *A61K 47/14* | (2017.01) | |
| *A61K 47/24* | (2006.01) | |
| *A61K 47/26* | (2006.01) | |
| *A61K 47/38* | (2006.01) | |

(52) U.S. Cl.
CPC .......... *A61K 31/4035* (2013.01); *A61K 47/14* (2013.01); *A61K 47/24* (2013.01); *A61K 47/26* (2013.01); *A61K 47/38* (2013.01)

(58) Field of Classification Search
CPC .................................................. A61K 31/4035
See application file for complete search history.

(56) References Cited

PUBLICATIONS

PubChem. "Chlorthalidone." (Nov. 30, 2010). Accessed Apr. 8, 2023. Available from: < https://pubchem.ncbi.nlm.nih.gov/compound/Chlorthalidone > . (Year: 2010).*
"Poloxamer 188." (May 17, 2018). Accessed on Apr. 8, 2023. Available from: < https://incidecoder.com/ingredients/poloxamer-188 >. (Year: 2018).*
Sidley Chemical. "Microcrystalline Cellulose (MCC)." (May 26, 2013). Accessed Apr. 8, 2023. Available from: < https://celluloseether.com/product/microcrystalline-cellulose-9004-36-6/ > . (Year: 2013).*
Making Cosmetics, Inc. "Hydroxypropylmethylcellulose." (Feb. 10, 2018). Accessed Apr. 9, 2023. Available from: < https://www.ulprospector.com/en/na/PersonalCare/Detail/34148/750837/Hydroxypropyl-Methylcellulose > . (Year: 2018).*
Acme Hardesty Co. "Propyl Paraben." (Apr. 15, 2015). Accessed Apr. 9, 2023. Available from: < https://www.ulprospector.com/en/na/PersonalCare/Detail/4237/121149/Propyl-Paraben >. (Year: 2015).*
KCC Basildon. "Simethicone Antifoam PD3OS." (Aug. 2017). Accessed Apr. 9, 2023. Available from: < https://www.kcc-basildon.com/wp-content/uploads/2017/11/PD30S.pdf >. (Year: 2017).*
"Sweetening agents for Pharmaceutical Preparations." (Nov. 5, 2019). Accessed Apr. 9, 2023. Available from: < https://pharmaeducation.net/sweetening-agents/ >. (Year: 2019).*

* cited by examiner

*Primary Examiner* — John S Kenyon
(74) *Attorney, Agent, or Firm* — Umberg Zipser LLP

(57) ABSTRACT

Compositions of a stabilized chlorthalidone suspension and methods for making a stabilized chlorthalidone suspension include chlorthalidone along with a solubilizing and/or wetting agent, a suspending agent, and a viscosity increasing agent and/or an anti-caking agent, wherein the stabilized chlorthalidone suspension is a uniform dispersion with consistent concentration of chlorthalidone throughout the composition and storage.

20 Claims, 45 Drawing Sheets

Fig. 1C

Add Mixture 1 colloidal solution to Mixture 2, stir with 2000 RPM for 15 minute

Add Flavor, stir with 2000 RPM for 15 min and Homogenize for 20 min

QS the batch volume, Homogenize for 20 minute and stir with 2000 RPM for 15 minute Chlorthalidone Oral Suspension 10 mg/mL Step – I Completed.

Fig. 1F

Step - III

Add Step-I colloidal solution to Step-II, stir with 2000 RPM for 30 minute

Add Flavor, Citric acid anhydrous stir with 2000 RPM for 120 min

QS the batch volume, and stir with 2000 RPM for 12 hour

Chlorthalidone Oral Suspension 5 mg/mL

Fig. 3A

| Step | Ingredients | HG Limit (mg/mL) | Range covered (mg/mL) | Final | T1 | T2 | T3 | T4 | T5 | TS_1 | TS_2 | TS_3 |
|---|---|---|---|---|---|---|---|---|---|---|---|---|
| Step-I | Water | QS | QS | Y | Y | Y | Y | Y | Y | Y | Y | Y |
| | Methyl Paraben | 200 | 1 | Y | Y | x | x | x | x | x | x | x |
| | Propyl Paraben | 40 | 0.2 | Y | Y | x | x | x | x | x | x | x |
| | Potassium Sorbate | 5 | | x | | | | | | | | |
| | Citric acid monohydrate | 14 | | x | | | | | | | | |
| | Polyethylene Glycol | 50 or 0.044 mL | 0.044 mL | P188 | PEG | | | | | | | |
| | Simethicone | 9 or 0.009 mL | 0.009 mL | Y | Y | Y | Y | Y | Y | Y | Y | Y |
| | Micro Crystalline Cellulose | 20 | 20 | Y | Y | x | Y | Y | Y | Y | Y | Y |
| | Sucrose | 500, 802.87 | 150 | Y | Y | x | x | Y | Y | Y | Y | Y |
| | Silicon Dioxide | 67.9 | 10, 20, 30 | Y | Y | x | x | x | x | | x | x |
| | Hydroxy Ethyl Cellulose | 0.25, 30 | 2 | Y | Y | x | x | x | x | | | Y |
| | 70% Sorbitol solution | 975 or 0.66 mL | 0.2 mL | Y | Y | x | x | x | x | | Y | Y |
| Step-II | Poloxamer 188 | 20 | 10 | PEG | P188 | x | Y | Y | Y | Y | Y | Y |
| | Chlorthalidone | NA | NA | Y | Y | Y | Y | Y | Y | Y | Y | Y |
| | Yellow color | 1 | 0.5 | Y | Y | x | x | x | x | x | x | x |
| | Strawberry flavor | 0.7 or 0.0086 mL / 1 or 0.001 mL / 2 or 0.002 mL | 0.001 mL | Y | Y | x | x | x | x | x | x | x |

P188 - Poloxamer 188, PEG - Polyethylene Glycol

Fig. 3B

| Step | Ingredients | HG Limit (mg/mL) | Range covered (mg/mL) | T2 | T3 | T4 | T5 | T5_1 | T5_2 | T5_3 |
|---|---|---|---|---|---|---|---|---|---|---|
| Step-I | Water | QS | QS | QS | QS | QS | QS | QS | QS | QS |
| | Simethicone | 9 or 0.009 mL | 0.009 mL | x | 0.009 mL | 0.009 mL | 0.009 mL | 0.009 mL | 0.009 mL | 0.009 mL |
| | Micro Crystalline Cellulose | 20 | 20 | 20 | 20 | 20 | 20 | 20 | 20 | 20 |
| | Sucrose | 500, 802.87 | 150 - 300 | x | x | 150 | 150 | 150 | 150 | 300 |
| | Glycerin | 574.11 | 200 | x | x | x | x | x | x | x |
| | Sucralose | 12 | 2.5 | x | x | x | 2.5 | 2.5 | 2.5 | 2.5 |
| | Hydroxy Ethyl Cellulose | 0.25, 30 | 0.25 - 2 | x | x | x | 2 | 2 | 0.25 | 0.25 |
| | Poloxamer 188 | 20 | 10 | x | 10 | 10 | 10 | 10 | 10 | 10 |
| Step-II | Chlorthalidone | NA | 5 | 5 | 5 | 5 | 5 | 5 | 5 | 5 |

Fig. 3C

| Trials | Change | Observations | | |
|---|---|---|---|---|
| | | For Step - I | For Step - II | Suspension |
| T2 | Only MCC used as a suspending agent in Step-I. | 1. After stirring, MCC settled immediately. 2. After homogenization, MCC gets uniformly distributed but no. of air bubble was observed in colloidal solution. | 1. After addition of CHL, floating of API was observed, which gets mixed after 5 minute of stirring. 2. During homogenization for 15 minutes, large foam was observed and also API gets settled immediately. | 1. Settlement rate was very high 1 mL/min for initial 5 minutes. 2. After 3 hours, 60 mL of clear layer was observed i.e. up to 40 mL of suspended particle found settled in 100 mL VF. |
| T3 | 1. Antifoaming agent added compare to T2 to remove air bubble. 2. P188 added in Step-II to get uniform dispersion of API. This also helps to improve suspending properties. | 1. Simethicone used as an antifoaming agent. Stirring cannot emulsify the Simethicone in water, so homogenize the Simethicone. 2. MCC gets well distributed in water after homogenization. Also air bubble form but gets disappear immediately. 3. Bitter in taste. | 1. P188 used here to increase wetting properties of API. But foam was observed during dissolving of P188. Hence here required emulsify solution of Simethicone. 2. No floating of API was observed. 3. API gets immediately dispersed in P188 solution. 4. API not get immediately settled compare to T2. | 1. No settlement was observed within 5 min. 2. 25 mL settlement was observed in 30 min. 3. 70 mL settlement was observed after 24 hours. |

Fig. 3D

| Trials | Change | Observations | | |
|---|---|---|---|---|
| | | For Step - I | For Step - II | Suspension |
| T4 | 1.Sucrose added in Step-I. | 1.No sweet taste.<br>2. Required to add one more sweetener. | 1.No foam was observed due to dispersion of API in Simethicone emulsify solution. | 1. Foam was observed during homogenization in 20 minute. Hence required 10-minute homogenization.<br>2. Air bubble was removed by stirring for 30 minutes with low RPM.<br>3. No settlement was observed within 5 min.<br>4. 10 mL settlement was observed in 30 min.<br>5. 65 mL settlement was observed after 24 hours.<br>6. Required to viscosity increasing agent such as HEC. |

Fig. 3E

| Trials | Change | Observations | | |
|---|---|---|---|---|
| | | For Step - I | For Step - II | Suspension |
| T5 | 1.Sucralose and HEC added in Step-I. | 1.Sweet taste. 2.No uniform dispersion of MCC was observed as MCC was added in viscous solution. It means that, the MCC needed first to disperse into emulsify solution then needed to add sweetening and viscosity increasing agent. | 1.Same as per T4. | 1. Foam was not observed during homogenization in 10 minute. 2. Air bubble was removed by stirring for 30 minutes with low RPM. 3. No settlement was observed within 5 min. 4. 10 mL settlement was observed in 6 hours. 5. 10 mL settlement was observed after 24 hours. 6.Required to change the excipient addition. |

Fig. 3F

| Trials | Change | Observations | | |
|---|---|---|---|---|
| | | For Step - I | For Step - II | Suspension |
| T5_1 | 1.Same as T5 2.Addition of excipient was changed. | 1.Sweet taste. 2.Uniform dispersion of MCC was observed. | 1.Same as per T4. | 1. No settlement was observed within 5 min. 2. No settlement was observed within 24 hours. 3. Required to reduce the quantity of HEC, as it used more than HG limit. |
| T5_2 | 1.Same as T5_1. 2.The quantity of HEC was changed from 2 mg/mL to 0.25 mg/mL. | 1.Same as T5_1. | 1.Same as T4. | 1. No settlement was observed within 5 minute. 2. 17 mL settlement was observed within 24 hours. 3. Needs to increase viscosity increasing agent. |
| T5_3 | 1.Same as T5_1 2.Sucrose quantity added as 300 mg/mL instead of 150 mg/mL. | 1.Same as T5_1. | 1.Same as T4. | 1. After homogenization for 10 minutes, suspension having more foam on the surface. 2. All foam and air bubble was removed by stirring at low RPM for 30 minutes. 3. 5 mL of suspension was settled after 2 hours. 4. 7 mL of suspension was settled after 65 hours. 5. Only sucralose can make a sweet suspension. Hence sucrose can be removed and another suspending agent such as glycerin, silicon dioxide and gum can be used. |

Fig. 3G

| Step | Ingredients | HG Limit (mg/mL) | Range covered (mg/mL) | TS | TS_1 | TS_2 | TS_3 | TS_4 200 mL | TS_5 200 mL | TS_6 500 mL | TS_7 500 mL | TS_8 500 mL_1 | TS_8 500 mL_2 | TS_9 500 mL_1 | TS_9 500 mL_2 |
|---|---|---|---|---|---|---|---|---|---|---|---|---|---|---|---|
| Step-I | Water | QS | QS | QS | QS | QS | QS | QS | QS | QS | QS | QS | QS | QS | QS |
| | Simethicone | 9 or 0.009 mL | 0.009 mL | 0.009 mL | 0.009 mL | 0.009 mL | 0.009 mL | 0.009 mL | 0.009 mL | 0.009 mL | 0.009 mL | 0.009 mL | 0.009 mL | 4.5 g | 4.5 g |
| | Micro Crystalline Cellulose | 20 | 20 | 20 | 20 | 20 | 20 | 20 | 20 | 20 | 20 | 20 | 20 | 20 | 20 |
| | Sucrose | 500, 802.57 | 150 - 300 | 150 | 150 | 150 | 300 | x | x | x | x | x | x | x | x |
| | Glycerin | 574.11 | 160 - 364 | x | x | x | x | 200 | x | x | x | 160 | 364 | 300 | 300 |
| | Silicon Dioxide | 67.9 | 20 - 30 | x | x | x | x | x | 20 | x | 30 | x | 20 | x | x |
| | Xanthan Gum | 13.75 | 0.4 - 5 | x | x | x | x | x | x | 5 | x | 0.8 | x | 0.4 | x |
| | Sucralose | 12 | 2.5 | 2.5 | 2.5 | 2.5 | 2.5 | 2.5 | 2.5 | 2.5 | 2.5 | 2.5 | 2.5 | 2.5 | 2.5 |
| | Hydroxy Ethyl Cellulose | 0.25, 30 | 0.25 - 2 | 2 | 2 | 0.25 | 0.25 | 0.25 | 0.25 | 0.25 | 0.25 | 0.25 | 0.25 | 0.25 | 0.25 |
| | Poloxamer 188 | 20 | 10 | 10 | 10 | 10 | 10 | 10 | 10 | 10 | 10 | 10 | 10 | 10 | 10 |
| Step-II | Chlorthalidone | NA | 5 | 5 | 5 | 5 | 5 | 5 | 5 | 5 | 5 | 5 | 5 | 5 | 5 |

Fig. 3H

| Trials | Change | Observations | | |
|---|---|---|---|---|
| | | For Step - I | For Step - II | Suspension |
| T5_4 | 1.Same as T5 2.Sucrose was removed and Glycerin was used as a sweetening and viscosity increasing agent. | 1.Sweet taste. 2.HEC added before Glycerin addition due to solid nature of HEC. | 1.Same as per T4. | 1. 22 mL settlement was observed within 60 min. 2. 63 mL settlement was observed within 24 hours. 3. Required to stir at low RPM to remove the foam. 4. Ross homogenizer was used; hence minimum batch size would require as 500 mL. This having impact on mixing and homogenization. |
| T5_5 | 1.Same as T5 2.Sucrose was removed and Silicon Dioxide was used as a viscosity increasing agent. | 1.It look like uniform distribution of MCC and Silicon dioxide in water. | 1.Same as per T4. | 1. 35 mL settlement was observed within 1 hour. 2. 35 mL settlement was observed in 24 hours. 3. Due to small batch size, homogenization may not be proper. Hence it require to increase batch size up to 500 mL. |
| T5_6 | 1.Same as T5 2.Sucrose was removed and Xanthan Gum was used as a viscosity increasing agent. | 1. After addition of Xanthan Gum, colloidal solution becomes very thick. Need to reduce the quantity of Xanthan Gum. | 1.Same as per T4. | 1. After homogenization also suspension was very thick and having no. of air bubble trapped in suspension. Due to this density cannot be measured. 2. After 24 hours also, suspension found as it is like initial. 3. Xanthan gum can be acts as an good viscosity agent by reducing its quantity. |

Fig. 31

| Trials | Change | Observations | | |
|---|---|---|---|---|
| | | For Step - I | For Step - II | Suspension |
| T5_7 | 1. Same as T5_5 2. Only quantity of Silicon dioxide was increased from 20 mg/mL to 30 mg/mL. 3. Batch size was changed from 200 mL to 500 mL. | 1.It look like uniform distributio n of MCC and Silicon dioxide in water. | 1.Same as per T4. | 1. 15 mL settlement was observed within 30 minutes. 2. After homogenization, very less air bubble was observed compare to T5_6. 3. Even though increase in concentration of Silicon dioxide cannot have more effect on viscosity of suspension. 4. In T5_1, there was no settlement was observed in 24 hours. In this trial, HEC was used as 2 mg/mL and Sucrose was used as 150 mg/mL. But HEC was used more compare to its IID limit. So HEC was used as 0.25 mg/mL and Sucrose was removed in T5_4, T5_5, T5_6 and T5_7. 5. In T5_2, there was 17 mL settlement in 24 hours. Here HEC used as 0.25 mg/mL and Sucrose used as 150 mg/mL. 6. In T5_3, there was 5 mL settlement in 2 hours and 7 mL settlement in 65 hours. Here HEC used as 0.25 mg/mL and Sucrose used as 300 mg/mL. 7. In T5_4, T5_5, T5_6 and T5_7, Sucrose was not used and settlement rate was more in all this trial compare to T5_1, T5_2 and T5_3. This shows that the Sucrose will helps for suspending the particles. |

Fig. 3J

| Trials | Change | Observations | | |
|---|---|---|---|---|
| | | For Step - I | For Step - II | Suspension |
| T5_8 | 1. Same as T5_5<br>2. 1000 mL of batch was planned. Divided into two part of 500 mL each.<br>3. In one part of 500 mL, 160 mg/mL of Glycerin and 0.8 mg/mL of Xanthan gum was used.<br>4. In another part of 500 mL, 364 mg/mL of Glycerin and 20 mg/mL of Silicon dioxide was used. | 1.Common MCC colloidal solution was prepared by using high 6500 RPM for 45 minutes, | 1.Same as per T4. | For Xanthan Gum containing suspension<br>1. Very thick suspension was observed. Hence needs to reduce the quantity of Xanthan Gum.<br>2. This suspension contains no. of air bubble. These air bubble removed in overnight stirring.<br>3. No settlement was observed in 24 hours.<br>For Silicon dioxide containing suspension<br>1. Within 30 minute, 50 mL of settlement was observed.<br>2. 50 mL of settlement was observed in 24 hours.<br><br>By comparing both suspension, it was clear that, Gum and Glycerin was needed to improve suspending property.<br>To prove that, next trial taken with only Glycerin and Glycerin with Xanthan Gum. |

Fig. 3K

| Trials | Change | Observations | | |
|---|---|---|---|---|
| | | For Step - I | For Step - II | Suspension |
| T5_9 | 1. Same as T5_5 2. 1000 mL of batch was planned. Divided into two part of 500 mL each. 3. In one part of 500 mL, 300 mg/mL of Glycerin and 0.4 mg/mL of Xanthan gum was used. 4. In another part of 500 mL, only 300 mg/mL of Glycerin was used. | 1.Common MCC colloidal solution was prepared by using high 6500 RPM for 45 minutes. | 1.Same as per T4. | For Xanthan Gum containing suspension 1. Final suspension required continuous stirring for 15 to 20 hours to make uniform suspension and remove any air bubble if present. 2. No settlement was observed in 24 hours. For only Glycerin containing suspension 1. 70 mL of settlement was observed in 24 hours. By comparing both suspension, it was clear that, Gum and Glycerin was needed to improve suspending property. |

Fig. 4A

STABILITY STUDY SUMMARY REPORT

Generic Name: Chlorthalidone Oral Suspension 10 mg/mL

| Batch No. | : NCH1972 | Packing Details | : Bottle : 12 OZ Amber PET Plastic Boston Round Bottles-3371B09-BABR (Berlin PACKAGING, Item # 3371B09-B) CAP : 24-410 White PP Plastic Screw Top Cap (Foam Liner), Item # X24-410 |
|---|---|---|---|
| Mfg. Date | : 09/2019 | Purpose of study | : Development Batch, Stability Study |
| Storage Condition | : 25°C ± 2°C & RH 60% ± 5% | API Details | : Chlorthalidone USP-EP Micronized, Batch No. # IF1500690A |
| Study started on | : 09/20/2019 | API manufacturer | : Euticals (Italy) |

FIG. 4A (cont'd)

| Test | Specification | | Initial | 3 Month | 6 Month |
|---|---|---|---|---|---|
| Description | Yellow uniform suspension with strawberry flavors. | | Complies | Complies | Complies |
| Identification test (By HPLC) | The retention time of the major peak in the chromatogram of the Assay preparation corresponds to that of the internal standard preparation, both relative to the internal standard, as obtained in the assay test. | | Complies | Complies | Complies |
| pH | Between 3.0 and 7.0 | | 5.21 | 4.87 | 4.76 |
| Specific Gravity | Between 1.0 to 1.3 | | 1.17 | 1.14 | 1.12 |
| Osmolarity (mOsm/kg) | For information only (*1:1 dilution with water) | | Not Performed | 1122 | 1109 |
| Dissolution (By HPLC) | Not less than 75% (Q) of labeled amount of Chlorthalidone is dissolves in 30 min. | Minimum | 100 % | 91 % | 93 % |
| | | Maximum | 102 % | 107 % | 99 % |
| | | Mean | 101 % | 102 % | 97 % |
| Related Substance (By HPLC) | Chlorthalidone Related Compound A : Not more than 0.7 % | | 0.45% | 0.39% | 0.37% |
| | Impurity I : Not more than 0.2 % | | 0.02% | BQL | 0.01% |
| | Impurity G : Not more than 0.7 % | | 0.11% | 0.11% | 0.10% |
| | CPSP : Not more than 0.10 % | | Not Detected | Not Detected | Not Detected |
| | Any individual unknown impurity : Not more than 0.20 % | | 0.06% | 0.05% | 0.02% |
| | Total impurities (Excluding Chlorthalidone Related Compound A) : Not more than 0.80 % | | 0.18% | 0.21% | 0.17% |
| Viscosity | 150 cps to 700 cps | | Not Performed | Not Performed | Not Performed |

Fig. 4B

STABILITY STUDY SUMMARY REPORT

Generic Name: Chlorthalidone Oral Suspension 10 mg/mL

| Batch No. | : NCH1972 | Packing Details | : Bottle : 12 OZ Amber PET Plastic Boston Round Bottles- 3371B09-BABR (Berlin PACKAGING, Item # 3371B09-B) CAP : 24-410 White PP Plastic Screw Top Cap (Foam Liner), Item # X24-410 |
|---|---|---|---|
| Mfg. Date | : 09/2019 | Purpose of study | : Development Batch, Stability Study |
| Storage Condition | : 25°C ± 2°C & RH 60% ± 5% | API Details | : Chlorthalidone USP-EP Micronized, Batch No. # IF1500690A |
| Study started on | : 09/20/2019 | API manufacturer | : Euticals (Italy) |

FIG.4B (cont'd)

| Assay | | Bottom-1 | Bottom-2 | Middle-1 | Middle-2 | Top-1 | Top-2 |
|---|---|---|---|---|---|---|---|
| Between 90.0% and 110.0% of labeled amount of Chlorthalidone | Initial | 106.3 | 106.9 | 107.0 | 106.4 | 106.5 | 106.5 |
| | 3 Month | 103.3 | 103.6 | 103.6 | 104.0 | 103.2 | 103.7 |
| | 6 Month | 102.6 | 102.5 | 102.4 | 101.7 | 102.0 | 102.4 |
| Between 85.0% and 115.0% of labeled amount of Methyl Paraben | Initial | 101.7 | 102.2 | 103.1 | 102.6 | 101.9 | 101.7 |
| | 3 Month | 99.9 | 100.1 | 99.5 | 100.8 | 99.4 | 99.9 |
| | 6 Month | 98.9 | 99.0 | 99.0 | 98.2 | 98.5 | 98.9 |
| Between 85.0% and 115.0% of labeled amount of Propyl Paraben | Initial | 99.8 | 100.7 | 100.2 | 99.9 | 99.6 | 98.6 |
| | 3 Month | 96.4 | 96.7 | 96.3 | 96.9 | 96.1 | 96.6 |
| | 6 Month | 97.9 | 97.8 | 97.9 | 97.0 | 97.5 | 97.9 |

FIG. 4C

| Generic Name: Chlorthalidone Oral Suspension 10 mg/mL | | Packing Details | Bottle: 12 OZ Amber PET Plastic Boston Round Bottles-9171855-BABR (Item PACKAG0015, Item # 1111854-E) |
|---|---|---|---|
| Batch No | NC01973 | | |
| Mfg. Date | 08/2019 | Purpose of study | C.P. 24 ±2 ℃ Wide PP Plastic Screw Top Cap Ream, Item # 2264-10 |
| Storage Condition | 25 ℃/3 ℃ & RH 60% ± 5% | API Details | Development Batch. Stability Study |
| Study started on | 09/20/2019 | API manufacturer | Chlorthalidone USP-EP Micronized, Batch No. # T915/05/PAA Ervum (USA) |

| Test | Specification | Initial | 3 Month | 6 Month |
|---|---|---|---|---|
| *Microbiological Examination | | | | |
| Microbial Enumeration Tests | Aerobic microbial count : Not more than 100 cfu/g | Not Performed | Not Performed | < 10 cfu/g |
| | Moulds and Yeasts : Not more than 10 cfu/g | Not Performed | Not Performed | < 10 cfu/g |
| Test for specified microorganisms | Salmonella species : Should be Absent/g | Not Performed | Not Performed | Not Detected |
| | Escherichia coli : Should be Absent/10g | Not Performed | Not Performed | Not Detected |
| Lab Notebook Reference / Page No | | 192038-128 192038-176,183 192033,18 | 192038-126,128,171,181 | 192046 - 28-32, 40-41, 50-61, 175, 33-39, 62-113, 176-184 |

NA = Not Applicable, ND = Not Detected, LOQ = Limit of Quantification, BQL = Below Quantification Limit
LOQ Limit: Chlorthalidone Related Compound A: 0.01%, Chlorthalidone: 0.01%, CPSP impurity: 0.01% & Impurity G: 0.01 %.
*Microbiological Examination result compiled as per Nelson Labs Report No. # R-566488-R0, R-573923-R0

FIG.4D

| Generic Name: Chlorthalidone Oral Suspension, 10 mg/mL | | Packaging Details: | Bottle: 30 OZ Amber PET Plastic Boston Round Bottles- AS71BSP-30-KGD (Berlin PACKAGING, Item # 33731809-B) | | |
|---|---|---|---|---|---|
| Batch No.: NCHS1971 | | | | | |
| Mfg. Date: 06/2019 | | Purpose of study: | Cap: 24/410 White PP Plastic Active Tab Cap (Global Lasan), Item # 5-14-416 | | |
| Storage Condition: 40°C ± 2°C & RH 75% ± 5% | | API Details: | Developmental Batch Stability Study | | |
| Study started on: 06/28/2019 | | SSF: 24mg/Biscuit | Chlorthalidone USP-XFI Micronized, Batch No. # BD160934, Kopran (API) | | |

| Test | Specification | | Initial | 3 Month | 6 Month |
|---|---|---|---|---|---|
| Description | Yellow uniform suspension with strawberry flavors. | | Complies | Complies | Complies |
| Identification test (By HPLC) | The retention time of the major peak in the chromatogram of the Assay preparations corresponds to that of the standard preparation, both relative to the internal standard, as obtained in the assay test. | | Complies | Complies | Complies |
| pH | Between 3.0 and 7.0 | | 5.21 | 4.48 | 4.23 |
| Specific Gravity | Between 1.0 to 1.3 | | 1.17 | 1.14 | 1.13 |
| Osmolality (mOsm./kg) | For information only (*1:1 dilution with water) | | Not Performed | 1183 | 1377 |
| Dissolution (By HPLC) | Not less than 75% (Q) of labeled amount of Chlorthalidone is dissolves in 30 min. | Minimum | 100 % | 80 % | 95 % |
| | | Maximum | 102 % | 104 % | 101 % |
| | | Mean | 101 % | 95 % | 99 % |
| Related Substances (By HPLC) | Chlorthalidone Related Compound A: Not more than 0.7 % | | 0.45% | 0.60 % | 0.51 % |
| | Impurity I: Not more than 0.2 % | | 0.02% | BQL | 0.01 % |
| | Impurity G: Not more than 0.2 % | | 0.11% | 0.11 % | 0.10 % |
| | CPSP: Not more than 0.10 % | | Not Detected | Not Detected | Not Detected |
| | Any individual unknown impurity: Not more than 0.20 % | | 0.05% | 0.04 % | 0.03 % |
| | Total impurities [Excluding Chlorthalidone Related Compound A]: Not more than 0.80 % | | 0.18% | 0.26% | 0.25 % |
| Viscosity | 150 cps to 300 cps | | Not Performed | Not Performed | Not Performed |

FIG. 4E

Generic Name: Chlorthalidone Oral Suspension 50 mg/mL
Batch No.: NC01977
Mfg. Date: 05/2019
Storage Condition: 40°C/75% RH & RT (25°C ± 2°C)
Study started on: 05/23/2019

Packing Details:
Bottles: 12 OZ Amber PET Plastic Bottles Round Bottles-33/400 BASR (Peko: PACKAGING, Item #: 3331BPB-B)
Cap: Quality White PP Ribbed-Smooth Top Cap (Foam Liner, Item #: XO4-446 Development Batch, Bulk No., Pack)
Stability Batch, Bulk No. # Unlabeled, Batch No. # IN-NMO44A
Bottle: Only

| Assay | | Bottom-1 | Bottom-2 | Middle-1 | Middle-2 | Top-1 | Top-2 |
|---|---|---|---|---|---|---|---|
| Between 90.0% and 110.0% of labeled amount of Chlorthalidone | Initial | 106.3 | 106.9 | 107.0 | 106.4 | 106.5 | 106.5 |
| | 3 Month | 102.2 | 102.6 | 101.8 | 101.5 | 101.8 | 102.8 |
| | 6 Month | 102.1 | 102.4 | 102.3 | 102.5 | 101.6 | 102.0 |
| Between 85.0% and 115.0% of labeled amount of Methyl Paraben | Initial | 101.7 | 102.3 | 102.1 | 102.0 | 101.9 | 101.7 |
| | 3 Month | 99.2 | 100.1 | 100.4 | 100.9 | 100.0 | 100.3 |
| | 6 Month | 99.3 | 99.7 | 99.7 | 99.9 | 98.9 | 99.2 |
| Between 85.0% and 115.0% of labeled amount of Propyl Paraben | Initial | 99.2 | 100.7 | 100.2 | 99.9 | 98.6 | 99.6 |
| | 3 Month | 96.2 | 98.5 | 97.3 | 97.8 | 96.7 | 97.3 |
| | 6 Month | 98.3 | 99.2 | 99.1 | 98.7 | 98.5 | 98.0 |

Fig. 4F

STABILITY STUDY SUMMARY REPORT

| Generic Name :Chlorthalidone Oral Suspension 10 mg/mL | | |
|---|---|---|
| Batch No. | : NCH1972 | Packing Details | : Bottle : 12 OZ Amber PET Plastic Boston Round Bottles-3371B09-BABR (Berlin PACKAGING, Item # 3371B09-B) CAP : 24-410 White PP Plastic Screw Top Cap (Foam Liner), Item # X24-410 |
| Mfg. Date | : 09/2019 | Purpose of study | : Development Batch, Stability Study |
| Storage Condition | : 40°C ± 2°C & RH 75% ± 5% | API Details | : Chlorthalidone USP-EP Micronized, Batch No. # IF1500690A |
| Study started on | : 09/20/2019 | API manufacturer | : Euticals (Italy) |

FIG.4F (Cont'd)

| Test | Specification | Initial | 3 Month | 6 Month |
|---|---|---|---|---|
| *Microbiological Examination | | | | |
| Microbial Enumeration Tests | Aerobic microbial count. Not more than 100 cfu/g. Moulds and Yeasts. Not more than 10 cfu/g | Not Performed Not Performed | <10 cfu/g <10 cfu/g | <10 cfu/g <10 cfu/g |
| Test for specified microorganisms | Salmonella species. Should be Absent/g Escherichia coli. Should be Absent/10g | Not Performed Not Performed | Not Detected Not Detected | Not Detected Not Detected |
| Lab Notebook Reference / Page No. | | 192038-128 192028-176,183 192033-18 | 192038-126,127,171,181 | 192045 - 28-32, 40-41, 50-61, 173, 33-39, 62-113, 176-184 |

NA = Not Applicable, ND = Not Detected, LOQ = Limit of Quantification, BQL = Below Quantification Limit
LOQ Limit: Chlorthalidone Related Compound A: 0.01%, Chlorthalidone: 0.01%, CPSP impurity: 0.01% & Impurity G: 0.01 %.
*Microbiological Examination result complied as per Nelson Labs Report No. = R-566458-R0, R-573922-R0

| Conclusion: All test results well within acceptance limits. | | |
|---|---|---|
| Prepared By: (Research Chemist) | Checked By: (Sr. Research Chemist) | Approved By: (Research Chemist-QA) |
| Date: | Date: | Date: |

FIG.5A

| Generic Name: Chlorthalidone Oral Suspension 10 mg/mL | | Packing Details | Bottles: 10 OZ Amber PET Plastic Bottles Round Bottles-NVT1859-BABR (Selin PACKAGING, Item # 157/1309-B) |
|---|---|---|---|
| Batch No. | WJC1076 | | CAP: 24-410 White PP Plastic Export Top Caps (Smart Liner), Item # 3234-03 |
| Mfg. Date | 10/-2019 | Purpose of Study | Development Batch Stability Study |
| Storage Condition | 25 C ± 2 C & 60 % ± 5 % | API Details | Chlorthalidone USP EP Micronized, Batch No.: HP216005A |
| Study Initiation Date | 03/06/2019 | API manufacturer | (xxxx xxxx) |

| Test | Specification | | Initial | 3 Month | 6 Month |
|---|---|---|---|---|---|
| Description | Yellow uniform suspensions with strawberry flavors. | | Complies | Complies | Complies |
| Identification test (By HPLC) | The retention time of the major peak in the chromatogram of the Assay preparation corresponds to that of the standard preparation, both relative to the internal standard, as obtained in the assay test | | Complies | Complies | Complies |
| pH | Between 5.0 and 7.0 | | 5.37 | 4.66 | 4.54 |
| Specific Gravity | Between 1.0 to 1.3 | | 1.13 | 1.13 | 1.12 |
| Osmolality (mOsm./kg) | For information only (*1:1 dilution with water) | | Not Performed | 1135 | 1195 |
| Dissolution (By HPLC) | Not less than 75% (Q) of labeled amount of Chlorthalidone is dissolves in 30 min. | Minimum | 106 % | 83 % | 90 % |
| | | Maximum | 103 % | 105 % | 95 % |
| | | Mean | 107 % | 101 % | 93 % |
| Related Substances (By HPLC) | Chlorthalidone Related Compound A: Not more than 0.7 % | | 0.41% | 0.41% | 0.39 % |
| | Impurity L: Not more than 0.2 % | | BQL | BQL | 0.01 % |
| | Impurity G: Not more than 0.10 % | | 0.11% | 0.13% | 0.11 % |
| | CRSC: Not more than 0.10 % | | Not Detected | Not Detected | Not Detected |
| | Any individual unknown impurity: Not more than 0.20 % | | 0.01% | 0.03% | 0.02 % |
| | Total impurities [Excluding Chlorthalidone Related Compound A]: Not more than 0.80 % | | 0.12% | 0.22% | 0.18 % |
| Viscosity | 150 cps to 700 cps | | Not Performed | Not Performed | Not Performed |

FIG. 5B

| Generic Name: Chlorthalidone Oral Suspension 10 mg/mL | | Packing Details | Bottles: 1.5 OZ Amber PET Plastic Bottles, Round Bottles- 3371809-BASK (Berlin PACKAGING, Item # 1741809-B) |
|---|---|---|---|
| Batch No.: NXM1979 | | | CAP: 24-410 White PP Plastic Screw Top Cap (Foam Liner), Item # X24-410 |
| Mfg. Date: 09/2019 | | Purpose of study | Development Batch Stability Study |
| Storage Condition: 25°C±2°C & RH 60% ± 5% | | API Details | Chlorthalidone USP HD Micronized, Batch No. # HD5059/A |
| Study started on: 09/25/2019 | | API manufacturer | Batelco (Italy) |

| Assay | | Bottom-1 | Bottom-2 | Middle-1 | Middle-2 | Top-1 | Top-2 |
|---|---|---|---|---|---|---|---|
| Between 90.0% and 110.0% of labeled amount of Chlorthalidone | Initial | 104.5 | 104.1 | 102.1 | 101.9 | 101.8 | 101.9 |
|  | 3 Month | 104.0 | 104.3 | 103.2 | 103.4 | 103.8 | 104.3 |
|  | 6 Month | 102.5 | 102.9 | 102.8 | 103.4 | 102.9 | 102.9 |
| Between 85.0% and 115.0% of labeled amount of Methyl Paraben | Initial | 102.3 | 102.5 | 100.1 | 100.5 | 100.2 | 99.9 |
|  | 3 Month | 102.6 | 102.9 | 101.8 | 101.9 | 102.6 | 103.0 |
|  | 6 Month | 100.5 | 100.9 | 100.7 | 101.0 | 99.9 | 100.5 |
| Between 85.0% and 115.0% of labeled amount of Propyl Paraben | Initial | 98.7 | 98.4 | 97.2 | 97.0 | 97.2 | 97.2 |
|  | 3 Month | 97.8 | 98.2 | 97.3 | 97.3 | 98.0 | 98.4 |
|  | 6 Month | 98.6 | 99.3 | 98.7 | 99.1 | 97.8 | 98.6 |

FIG.5C

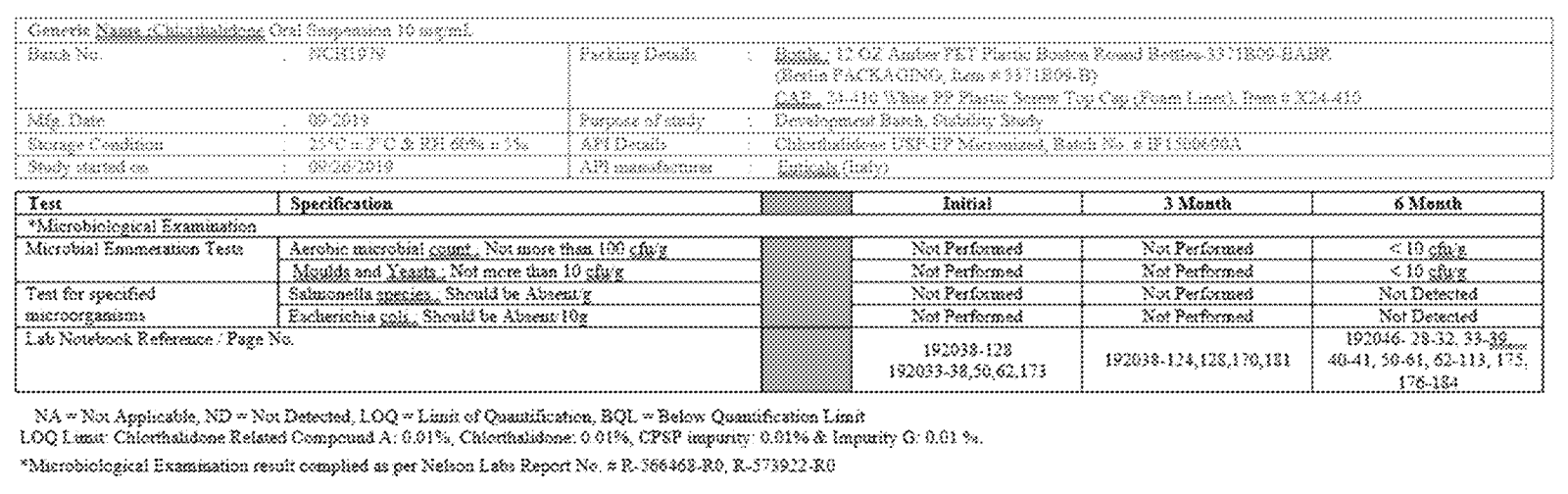

| Generic Name: Chlorthalidone Oral Suspension 10 mg/ml | | Packing Details | Bottle: 12 OZ Amber PET Plastic Boston Round Bottles, 33/1809-BARR (Item #:CFK-ACDO, Item #571809-B) Cap: 28-410 White PP Plastic Smrr TE Cap (Foam Liner), Item #: X24-410 |
|---|---|---|---|
| Batch No.: NCH1919 | | | |
| Mfg. Date: 09/2019 | | Purpose of study: | Benchmark Batch, Stability Study |
| Storage Condition: 25°C/60% & 30°C/65% ± 5 % | | API Details: | Chlorthalidone USP, UP Micronized, Batch No. # BV5106505A |
| Study Started on: 09/26/2019 | | | British (1969) |

| Test | Specification | Initial | 3 Month | 6 Month |
|---|---|---|---|---|
| *Microbiological Examination | | | | |
| Microbial Enumeration Tests | Aerobic microbial count: Not more than 100 cfu/g | Not Performed | Not Performed | < 10 cfu/g |
| | Moulds and Yeasts: Not more than 10 cfu/g | Not Performed | Not Performed | < 10 cfu/g |
| Test for specified microorganisms | Salmonella species: Should be Absent/g | Not Performed | Not Performed | Not Detected |
| | Escherichia coli: Should be Absent/10g | Not Performed | Not Performed | Not Detected |
| Lab Notebook Reference / Page No. | | 192038-123 192033-38,50,62,173 | 192038-124,123,170,181 | 192046, 28-32, 32-36, 40-41, 50-64, 62-113, 173, 178-183 |

NA = Not Applicable, ND = Not Detected, LOQ = Limit of Quantification, BQL = Below Quantification Limit
LOQ Limit: Chlorthalidone Related Compound A: 0.01%, Chlorthalidone: 0.01%, CPSP impurity: 0.01% & Impurity G: 0.01 %.
*Microbiological Examination result compiled as per Nelson Labs Report No. = R-586468-R0, R-573922-R0

FIG.5D

Generic Name : Chlorthalidone Oral Suspension, 10 mg/mL
Batch No : RC03199S

| Mfg. Date | 09/2019 | Packing Details | Bottle : 12-OZ Amber PET Plastic Boston Round Bottles-33/TB09-BARK (Bethe PACKAGING, Item # 33TB09-B) |
| Storage Condition | 40°C ± 2°C / 75 ± 5% RH | | CAP : 28-410 White PP Plastic Extra Top Cap (Comar Lot/P, Item # X16-410) |
| Study tested by | AUROBINDO | | Dropper/Pipette Batch, Blubaby Birds |
| | | Purpose of study | Chlorthalidone USP RS Monohydrate, Batch No. # R135693A |
| | | API Details | Batch Qty |

| Test | Specification | | | | Initial | 3 Month | 6 Month** |
|---|---|---|---|---|---|---|---|
| Description | Yellow uniform suspension with strawberry, flavors. | | | | Complies | Complies | Complies |
| Identification test (By HPLC) | The retention time of the major peak in the chromatogram of the Assay preparation corresponds to that of the external standard preparation, both relative to the external standard, as obtained in the assay test. | | | | Complies | Complies | Complies |
| pH | Between 3.9 and 7.0 | | | | 5.7 | 4.27 | 3.96 |
| Specific Gravity | Between 1.0 to 1.3 | | | | 1.13 | 1.14 | 1.12 |
| Osmolality (mOsm/kg) | For information only (*1:1 dilution with water) | | | | Not Performed | 1243 | 1392 |
| Dissolution (By HPLC) | Not less than 75% (Q) of labeled amount of Chlorthalidone is dissolves in 30 min. | | Minimum | | 106 % | 89 % | 94 % |
| | | | Maximum | | 108 % | 103 % | 98 % |
| | | | Mean | | 107 % | 99 % | 96 % |
| Related Substance (By HPLC) | Chlorthalidone Related Compound A : Not more than 0.7 % | | | | 0.41% | 0.56 % | 0.49% |
| | Impurity J : Not more than 0.2 % | | | | BQL | BQL | 0.01 % |
| | Impurity G : Not more than 0.2 % | | | | 0.11% | 0.10 % | 0.11 % |
| | CP&P : Not more than 0.10 % | | | | Not Detected | Not Detected | Not Detected |
| | Any individual unknown impurity : Not more than 0.20 % | | | | 0.01% | 0.04 % | 0.02 % |
| | Total impurities (Excluding Chlorthalidone Related Compound A) : Not more than 0.80 % | | | | 0.12% | 0.24 % | 0.23 % |
| Viscosity | 150 cps to 700 cps | | | | Not Performed | Not Performed | Not Performed |

FIG.5E

| Generic Name : Chlorthalidone Oral Suspension 10 mg/mL | | Packing Details | Bottle: 32 CC Amber PET Plastic Bottles Round Bottles-5573856-R356 (Bottle PACKAGING), Item # 78103809-B) Cap: 28-410 White PP Plastic Screw Top Cap (Foam Liner), Item # YCL-110 | | | | | |
|---|---|---|---|---|---|---|---|---|
| Batch No. | AS3819/19 | | | | | | | |
| Mfg. Date | 08/2019 | Purpose of Study | Development Batch, Stability Study | | | | | |
| Storage Condition | 40°C ± 2°C, RH 75% ± 5% | Specification | Chlorthalidone USP SP Monograph, Batch No. # AS3/2020/A | | | | | |
| Study started on | 08/28/2019 | API manufacturer | | | | | | |

| Assay | | Bottom-1 | Bottom-2 | Middle-1 | Middle-2 | Top-1 | Top-2 |
|---|---|---|---|---|---|---|---|
| Between 90.0% and 110.0% of labeled amount of Chlorthalidone | Initial | 104.5 | 104.1 | 102.1 | 101.9 | 101.8 | 101.9 |
| | 3 Month | 102.5 | 102.5 | 103.8 | 103.1 | 103.2 | 104.1 |
| | 6 Month | 102.7 | 102.8 | 101.6 | 102.1 | 102.2 | 103.2 |
| Between 85.0% and 115.0% of labeled amount of Methyl Paraben | Initial | 102.9 | 102.3 | 100.1 | 100.0 | 100.2 | 99.9 |
| | 3 Month | 102.5 | 102.1 | 102.4 | 102.8 | 101.4 | 101.9 |
| | 6 Month | 102.5 | 102.4 | 100.4 | 100.9 | 101.8 | 102.0 |
| Between 85.0% and 115.0% of labeled amount of Propyl Paraben | Initial | 98.7 | 99.4 | 97.2 | 97.0 | 97.2 | 97.2 |
| | 3 Month | 98.1 | 98.3 | 98.6 | 98.9 | 99.5 | 100.0 |
| | 6 Month | 101.3 | 101.3 | 99.3 | 99.9 | 100.2 | 100.8 |

FIG. 5F

| | | Packing Details | : Bottle: 15 OZ Amber PET Plastic Bottles, Round Bottles 33 T/BG2-SRRF<br>(Bottles PACK-AGHM#, Item # 311-0309-33)<br>Cap: 33-410 White PP Plain, Smooth Top Jazz (Plastic Lined, Item # ICDA-43) | | |
|---|---|---|---|---|---|
| Generic Name : Chlorthalidone Oral Suspension 10 mg/mL | | | | | |
| Batch No. : NC03/19 | | | | | |
| Mfg. Date : 05/2019 | | Purpose of study : Development Batch, Stability Study | | | |
| Storage Condition : 30°C ± 2°C & RH 75 % ± 5% | | API Details: Chlorthalidone USP-IP Micronized, Batch No. # BT/2026905A | | | |
| Shelf model life : 18 months (24 m) | | API manufacturer: Beryls (India) | | | |
| Test | Specification | | Initial | 3 Month | 6 Month |
| *Microbiological Examination<br>Microbial Enumeration Tests | Aerobic microbial count : Not more than 100 cfu/g | | Not Performed | <10 cfu/g | <10 cfu/g |
| | Moulds and Yeasts : Not more than 10 cfu/g | | Not Performed | <10 cfu/g | <10 cfu/g |
| Test for specified microorganisms | Salmonella species : Should be Absent/g | | Not Performed | Not Detected | Not Detected |
| | Escherichia coli : Should be Absent/10g | | Not Performed | Not Detected | Not Detected |
| Lab Notebook Reference / Page No. | | | 192038-138<br>192053-38,59,62,173 | 192038-123,128,179,181 | 192046- 12,15, 33-39,<br>40-41, 59-61, 62-113, 175,<br>176,184 |

NA = Not Applicable, ND = Not Detected, LOQ = Limit of Quantification, BQL = Below Quantification Limit
LOQ Limit: Chlorthalidone Related Compound A: 0.01%, Chlorthalidone: 0.01%, CPSP impurity: 0.01% & Impurity G: 0.01 %.
*Microbiological Examination result complied as per Nelson Labs Report No. = R-766446-R0, R-573922-R0
** Slightly yellowish white uniform suspension with strawberry flavor.

FIG.6A

| Generic Name: Chlorthalidone Oral Suspension 10 mg/mL | | | | | |
|---|---|---|---|---|---|
| Batch No.: N180563 | | Product Details | Bottle: 100 cc Boston Round Shape PET Bottle, A4-4W-07 GAMMA PACKAGING, Dummins Rd.,BHIDUPLAMS-610 Cap: TADO 2000 0 20/400 PP/PE Liner, GOLD RITE PLASTICS, Drawings No.CO24-16130 | | |
| Mfg. Date: 10/2019 | | Process of study: Stressed Batch Stability Study | | | |
| Storage Condition: 25°C ± 2°C & RH 60% ± 5% | | API Details: Chlorthalidone USP, SD Mercsdeal, Batch No. # BHC0060A | | | |
| Study: 6M | | | | | |

| Test | Specification | | Initial Complies | 3 Month Complies | 6 Month Complies |
|---|---|---|---|---|---|
| Description | Yellow uniform suspension with strawberry flavor. | | Complies | Complies | Complies |
| Identification test (By HPLC) | The retention time of the major peak in the chromatogram of the Assay preparation corresponds to that of the internal standard, as obtained in the assay test. | | | | |
| pH | Between 3.0 and 7.0 | | 5.34 | 4.76 | 4.50 |
| Specific Gravity | Between 1.0 to 1.5 | | 1.17 | 1.13 | 1.12 |
| Osmolality (mOsm/kg) | For information only (*1:1 dilution with water) | | Not Performed | 1051 | 1269 |
| Dissolution (By HPLC) | Not less than 75% (Q) of labeled amount of Chlorthalidone is dissolves in 30 min | Minimum | 102 % | 88 % | 87 % |
| | | Maximum | 108 % | 101 % | 97 % |
| | | Mean | 105 % | 96 % | 92 % |
| Related Substances (By HPLC) | Chlorthalidone Related Compound A: Not more than 0.7 % | | 0.33 % | 0.37 % | 0.35 % |
| | Impurity L: Not more than 0.2 % | | BQL | BQL | 0.01 % |
| | Impurity G: Not more than 0.2 % | | 0.11 % | 0.10 % | 0.10 % |
| | CPSE: Not more than 0.10 % | | Not Detected | Not Detected | Not Detected |
| | Any individual unknown impurity: Not more than 0.29 % | | 0.01 % | 0.04 % | 0.01 % |
| | Total impurities [Excluding Chlorthalidone Related Compound A]: Not more than 0.80 % | | 0.12 % | 0.18 % | 0.17 % |
| Viscosity | 150 cps to 700 cps | | Not Performed | Not Performed | Not Performed |

FIG.6B

| Container Name: Chlorthalidone Oral Suspension 50 mg/mL | | Packing Details | Bottles: 32 OZ Boston Round Shape PET Bottle, 24-410 CT (ALPHA PACKAGING, Drawing No# DWG1AP0248420) Cap: 24-410 CRC ASSM PET/D Logo Gold RITE PLASTICS, Drawing No. CQA-1045/B) |  |  |  |  |
|---|---|---|---|---|---|---|---|
| Batch No: NK93/094 | | | | | | | |
| Mfg. Date: 10/2019 | | Purpose of study: Development Zone Stability Study | | | | | |
| Storage Conditions: 25°C ± 2°C & RH 40% ± 5% | | API Details: Chlorthalidone USP/ IH Micronized, Batch No. AT15/0349A | | | | | |
| Study started on: 09/27/2019 | | APO manufactured: Biolyok (Italy) | | | | | |

| Assay | | Bottom-1 | Bottom-2 | Middle-1 | Middle-2 | Top-1 | Top-2 |
|---|---|---|---|---|---|---|---|
| | | Initial | | | | | |
| Between 90.0% and 110.0% of labeled amount of Chlorthalidone | | 99.9 | 100.2 | 100.0 | 100.3 | 99.3 | 99.7 |
| | | 3 Month | | | | | |
| | | 98.0 | 97.9 | 98.5 | 99.7 | 97.0 | 97.2 |
| | | 6 Month | | | | | |
| | | 97.4 | 97.7 | 97.5 | 97.7 | 97.4 | 97.5 |
| | | Initial | | | | | |
| Between 85.0% and 115.0% of labeled amount of Methyl Parabens | | 101.3 | 101.4 | 101.3 | 101.3 | 100.7 | 101.0 |
| | | 3 Month | | | | | |
| | | 95.9 | 96.7 | 98.7 | 98.6 | 95.1 | 96.2 |
| | | 6 Month | | | | | |
| | | 96.5 | 97.0 | 96.7 | 96.3 | 96.5 | 96.8 |
| | | Initial | | | | | |
| Between 85.0% and 115.0% of labeled amount of Propyl Parabens | | 98.2 | 98.3 | 98.0 | 98.4 | 97.5 | 97.8 |
| | | 3 Month | | | | | |
| | | 91.5 | 91.8 | 93.3 | 93.4 | 91.0 | 91.3 |
| | | 6 Month | | | | | |
| | | 94.0 | 94.7 | 94.2 | 94.4 | 94.1 | 94.3 |

FIG.6C

| Generic Name: Mometasone / Chlorothiazide Oral Suspension, 10 mg/mL | | Packing Details | | |
|---|---|---|---|---|
| Batch No: N0493M4 | | Bottle: 1 X 60 ml Amber Round shape PET Bottle, M-416677 ALPHA PACKAGING, Drawing No. 278811-AP-SM060 | | |
| Mfg. Date: 10/2019 | Purpose of study: | Cap: 24-400 CT Cap of SSC PP TO 56C GOLD PP/PE PLASTISOL, Drawing No. CGA-19050 | | |
| Storage Condition: 25°C & RH 60% ± 5% | R/D Details: | Development Batch, Stability Study | | |
| Study research No: | API manufacturer: | Chlorothiazide USP BP Mahmood, Batch No. # FY1506586A | | |
| | | Mometasone (NA) | | |

| Test | Specification | Initial | 3 Month | 6 Month |
|---|---|---|---|---|
| *Microbiological Examination | | | | |
| Microbial Enumeration Tests | Aerobic microbial count: Not more than 100 cfu/g | Not Performed | Not Performed | <10 cfu/g |
| | Moulds and Yeasts: Not more than 10 cfu/g | Not Performed | Not Performed | <10 cfu/g |
| Test for specified microorganisms | Salmonella species: Should be Absent/g | Not Performed | Not Performed | Not Detected |
| | Escherichia coli: Should be Absent/1g | Not Performed | Not Performed | Not Detected |
| Lab Notebook Reference - Page No. | | 192G38-128 192G33-143,153,165,170 | 192G38 - 104,122,128,169,183 | 192G46 - 28-32, 40-41, 50-61, 171, 73-79, G-111,126,181 |

NA = Not Applicable, ND = Not Detected, LOQ = Limit of Quantification, BQL = Below Quantification Limit
LOQ Limit: Chlorthalidone Related Compound A: 0.01%, Chlorthalidone: 0.01%, CPSP impurity: 0.01% & impurity G: 0.01 %
*Microbiological Examination result compiled as per Nelson Labs Report No. # R-573922-R0

Conclusion: All test results well within acceptance limits.

FIG.6D

| Generic Name: Chlorthalidone Oral Suspension 10 mg/mL | | | | | |
|---|---|---|---|---|---|
| Batch No.: RS03/004 | | Packing Details: Bottle: 1 × 60 Oz Boston Round Shape PET Bottle, 24-410 CT (ALPHA PACKAGING, Drawing No CDP71-0-C/L-016110)<br>Cap: 24-410 CPC A SSM PICTO Logo IMOLD RIBB PLASTICS, Drawing No CQA-10190)<br>Desiccant: Silica Gel<br>Closure: Chlorthalidone CIP EP Natcoprint Batch No. # IPTCHO04A<br>Pouch: Foil | | | |
| Mfg. Date: 10/2019 | | Purpose of study: | | | |
| Storage Condition: 40°C ± 2°C & RH 60% ± 5% | | API Details: | | | |
| Study Started on: 10/25/2019 | | API manufacturer: | | | |

| Test | Specification | | Initial<br>Complies | 3 Month<br>Complies | 6 Month<br>** |
|---|---|---|---|---|---|
| Description | Yellow uniform suspension with strawberry flavor. | | Complies | Complies | Complies |
| Identification test<br>(By HPLC) | The retention time of the major peak as the chromatogram of the Assay preparation corresponds to that of the internal standard preparation, both relative to the internal standard, as obtained in the assay test. | | Complies | Complies | Complies |
| pH | Between 3.0 and 7.0 | | 5.34 | 4.13 | 3.80 |
| Specific Gravity | Between 1.0 to 1.3 | | 1.17 | 1.13 | 1.13 |
| Osmolality (mOsm/kg) | For information only (*1:1 dilution with water) | | Not Performed | 1170 | 1435 |
| Dissolution<br>(By HPLC) | Not less than 75% (Q) of labeled amount of Chlorthalidone is dissolves in 30 min | Maximum | 102 % | 97 % | 97 % |
| | | Maximum | 108 % | 104 % | 98 % |
| | | Mean | 101 % | 97 % | 94 % |
| Related Substance<br>(By HPLC) | Chlorthalidone Related Compound A : Not more than 0.2 % | | 0.39 % | 0.50 % | 0.46 % |
| | Impurity J : Not more than 0.2 % | | BQL | BQL | 0.01 % |
| | Impurity O : Not more than 0.2 % | | 0.13 % | 0.13 % | 0.10 % |
| | CPSP : Not more than 0.10 % | | Not Detected | Not Detected | Not Detected |
| | Any individual unknown impurity : Not more than 0.20 % | | 0.01 % | 0.03 % | 0.02 % |
| | Total impurities (Excluding Chlorthalidone Related Compound A): Not more than 0.30 % | | 0.13 % | 0.22 % | 0.22 % |
| Viscosity | 150 cps to 700 cps | | Not Performed | Not Performed | Not Performed |

FIG. 6E

| Generic Name & Specification Oral Suspension 10 mg/mL | | Package Details | Bottle: 13 OZ Bottom Round Shape PET Bottle, 24.4-415 C7 (ALPHA PACKAGING, Drawing No. MDB1072-0663) |
|---|---|---|---|
| Batch No. | PCB10994 | | Cap: 24.410 CTC ASRA PICTO Logo (AKLD RTP PLASTICS, Drawing No. CQA-0135) |
| Mfg. Date | 03/19 | Dosage A 50ccy | Desiccant Bottle: Sorb-It, None |
| Storage Conditions | 40°C/75% RH Stability, 6M | API Details | Child Resistant: DTP BT Mechanical, Batch No. 2 BTS000JA |
| Study Start On | 06/01/2019 | | Insert: None |

| Assay | | Bottom-1 | Bottom-2 | Middle-1 | Middle-2 | Top-1 | Top-2 |
|---|---|---|---|---|---|---|---|
| Between 85.0% and 115.0% of labeled amount of Chlorthalidone | Initial | 98.9 | 100.2 | 100.0 | 100.3 | 99.4 | 99.7 |
| | 3 Month | 97.4 | 97.7 | 96.8 | 98.2 | 97.3 | 97.9 |
| | 6 Month | 96.6 | 96.5 | 96.8 | 96.9 | 97.2 | 97.4 |
| Between 85.0% and 115.0% of labeled amount of Methyl Paraben | Initial | 101.2 | 101.4 | 101.3 | 101.5 | 100.7 | 101.0 |
| | 3 Month | 97.2 | 97.5 | 96.5 | 97.9 | 97.3 | 97.7 |
| | 6 Month | 96.2 | 96.2 | 95.9 | 96.1 | 96.1 | 96.8 |
| Between 85.0% and 115.0% of labeled amount of Propyl Paraben | Initial | 98.2 | 98.3 | 98.0 | 98.4 | 97.5 | 97.8 |
| | 3 Month | 93.8 | 93.9 | 95.1 | 94.5 | 94.0 | 94.3 |
| | 6 Month | 95.7 | 95.5 | 95.2 | 95.5 | 95.8 | 96.1 |

FIG.6F

| Generic Name | Chlorthalidone Oral Suspension 10 mg/mL | Packing Details | Bottle: 3.3 Oz Boston Round Shape PET Bottle, 24-410 CT (ALPHA PACKAGING, Drawing No.DRPAP-SM419) |
|---|---|---|---|
| Batch No. | NC010954 | | CAP: 24-400 CRC ANSI PICO Logo (MILD RITE PLASTICS, Drawing No.CQA-10155) |
| Mfg. Date | 10/2019 | Purpose of study | Development Batch, Stability Study |
| Storage Condition | 40°C ± 2°C & RH 60% ± 5% | API Details | Chlorthalidone USP (IP Macromedical, Batch No.=BI19/00594 |
| Study started on | 10/08/2019 | API manufacturer | Lukoils (Italy) |

| Test | Specification | Initial | 3 Month | 6 Month |
|---|---|---|---|---|
| *Microbiological Examinations | | | | |
| Microbial Enumeration Tests | Aerobic microbial count : Not more than 100 cfu/g | Not Performed | <10 cfu/g | <10 cfu/g |
| | Moulds and Yeasts : Not more than 10 cfu/g | Not Performed | <10 cfu/g | <10 cfu/g |
| Test for specified microorganisms | Salmonella species : Should be Absent/g | Not Performed | Not Detected | Not Detected |
| | Escherichia coli : Should be Absent/10g | Not Performed | Not Detected | Not Detected |
| Lab Notebook Reference / Page No. | | 192038-133<br>192533-143,151,165,170 | 192035 –<br>104,122,128,169,181 | 192N46 – 28-32, 40-41, 56-61, 174, 33-39, 62-113, 176,184 |

NA = Not Applicable, ND = Not Detected, LOQ = Limit of Quantification, BQL = Below Quantification Limit
LOQ Limit: Chlorthalidone Related Compound A: 0.01%, Chlorthalidone: 0.01%, CPSP impurity: 0.01% & Impurity G: 0.01 %
*Microbiological Examination result complied as per Nelson Labs Report No. # R-566465-R0, R-573922-R0
** Slightly yellowish white uniform suspension with strawberry flavors.

FIG.7A

| Generic Name: Chlorthalidone Oral Suspension 1 mg/mL | | | Packing Details | : Bottles, 15 OZ Boston Round Shape, PET Bottle, 34-410 CT (ALPHA PACKAGING, Drawing No.HP31AP7-04410)<br>CAP, 34-400 CRC ASN1 PICTO-app AS/LD RIB PLASTICS, Drawing No.CO-16195) | | | |
|---|---|---|---|---|---|---|---|
| Batch No. | : NCHP03 | | Purpose of study | : Drop Test Study | | | |
| Mfg. Date | : 1/2018 | | API Details | : Chlorthalidone USP BP Micronized, Batch No. # 071086MA | | | |
| Storage Conditions | : 25°C ± 2°C & RH 60% ± 5% | | | | | | |
| Study Period No. | : 6 months | | | | | | |

| Test | Specification | | | Initial | 1 Month | 3 Month | 6 Month |
|---|---|---|---|---|---|---|---|
| Description | Yellow, uniform suspension with strawberry flavor. | | | Complies | Complies | Complies | Complies |
| Identification test (By HPLC) | The retention time of the major peak in the chromatogram of the Assay preparation corresponds to that of the internal standard preparation, both relative to the internal standard, as obtained in the assay test. | | | Complies | Complies | Complies | Complies |
| pH | Between 5.0 and 7.0 | | | 5.32 | 5.15 | 4.70 | 4.45 |
| Specific Gravity | Between 1.0 to 1.3 | | | 1.15 | 1.13 | 1.12 | 1.12 |
| Osmolality (mOsm / kg) | For information only (*1:1 dilution with water) | | | 1086 | 1066 | 1126 | 1089 |
| Dissolution (By HPLC) | Not less than 75% (Q) of labeled amount of Chlorthalidone is dissolves in 30 min. | Minimum | | 81 % | 88 % | 84.5 % | 93 % |
| | | Maximum | | 100 % | 102 % | 98 % | 97 % |
| | | Mean | | 96 % | 100 % | 96 % | 95 % |
| Related Substance (By HPLC) | Chlorthalidone Related Compound A : Not more than 0.7 % | | | 0.42% | 0.35 % | 0.28 % | Not Performed |
| | Impurity J : Not more than 0.2 % | | | 0.01% | BQL | 0.02 % | Not Performed |
| | Impurity G : Not more than 0.2 % | | | 0.11% | 0.09 % | 0.08 % | Not Performed |
| | CPSP : Not more than 0.10 % | | | Not Detected | Not Detected | Not Detected | Not Performed |
| | Any individual unknown impurity : Not more than 0.20 % | | | 0.05% | 0.03 % | 0.02 | Not Performed |
| | Total impurities (Excluding Chlorthalidone Related Compound A) : Not more than 0.80 % | | | 0.25% | 0.17 % | 0.15 % | Not Performed |
| Viscosity | 150 cps to 700 cps | | | Not Performed | Not Performed | Not Performed | Not Performed |

FIG.7B

| | | | | | | | |
|---|---|---|---|---|---|---|---|
| Generic Name: Chlorthalidone Oral Suspension 5 mg/ml | | Studies: 12 OZ. Reverse Round Clear PET Bottle, 23-410 CT ALPHA PACK A82NG, Closure No. PBBAP403402G CAP, 24-446 CRC ASSM PICO, and AKLO RITE PLASTICS, Drawing No. CGA-0156. Deep Green Black, Stability Sealing Chlorthalidone USP, BP Micronized, Batch No.: 4-HTM649A, Lot no. 4687 | | | | | |
| Batch No.: NCH9702 | | Packing Details | | | | | |
| Mfg. Date: 1/2015 | | | | | | | |
| Storage Conditions: 25°C ± 2°C & RH 60% ± 5% | | Degree of work: | | | | | |
| Study started on: 1/20/2015 | | API Details: API manufacturer: | | | | | |
| | | | Bottom-1 | Bottom-2 | Middle-1 | Middle-2 | Top-1 | Top-2 |
| | | | | | Initial | | | |
| Assay | Between 96.0% and 110.0% of labeled amount of Chlorthalidone | | 100.4 | 100.3 | 100.3 | 100.3 | 98.7 | 99.3 |
| | | | | | 1 Month | | | |
| | | | 100.2 | 100.6 | 100.9 | 100.7 | 100.3 | 100.7 |
| | | | | | 3 Month | | | |
| | | | 100.7 | 101.1 | 100.6 | 99.3 | 101.1 | 100.3 |
| | | | | | 6 Month | | | |
| | | | 98.5 | 98.0 | 98.2 | 97.8 | 98.0 | 97.6 |
| | Between 85.0% and 115.0% of labeled amount of Methyl Paraben | | Bottom-1 | Bottom-2 | Middle-1 | Middle-2 | Top-1 | Top-2 |
| | | | | | Initial | | | |
| | | | 98.8 | 97.8 | 97.9 | 98.1 | 97.4 | 97.3 |
| | | | | | 1 Month | | | |
| | | | 98.5 | 98.9 | 98.5 | 99.0 | 98.2 | 99.0 |
| | | | | | 3 Month | | | |
| | | | 98.8 | 99.1 | 98.4 | 97.2 | 99.1 | 98.4 |
| | | | | | 6 Month | | | |
| | | | 96.8 | 96.4 | 96.6 | 95.9 | 96.4 | 96.0 |
| | Between 85.0% and 115.0% of labeled amount of Propyl Paraben | | Bottom-1 | Bottom-2 | Middle-1 | Middle-2 | Top-1 | Top-2 |
| | | | | | Initial | | | |
| | | | 96.9 | 96.3 | 96.9 | 97.2 | 96.4 | 98.4 |
| | | | | | 1 Month | | | |
| | | | 97.8 | 97.6 | 98.9 | 97.7 | 97.5 | 97.8 |
| | | | | | 3 Month | | | |
| | | | 96.8 | 97.1 | 96.3 | 94.8 | 97.3 | 96.4 |
| | | | | | 6 Month | | | |
| | | | 95.4 | 94.6 | 94.9 | 94.0 | 94.7 | 94.4 |

FIG.7C

| | | | | | |
|---|---|---|---|---|---|
| Generic Name : Chlordiazepoxide Oral Suspension 5 mg/ml | | Packing Details | Bottle: 10 OZ Boston Round Amber PET Bottle, 24-410 CT (ALPHA PACKAGING, Item no. BOR10BAP2484108) Cap: 24-406 CRC ASSM PICCO Foam Gold RBTB BLACKTNX, Pressure No: CQA-011170 | | |
| Batch No. | RSH18103 | | | | |
| Mfg. Date | 12/2019 | Purpose of study | Development Batch, Stability Study | | |
| Storage Condition | 30 °C ± 2 °C & RH 65% ± 5% | | Chlordiazepoxide USP IP Micronized, Batch No. # FCQ6060A | | |
| Study Started on | 12/20/2019 | | API manufacturer | | |

| Test | Specifications | Initial | 1 Month | 3 Month | 6 Month |
|---|---|---|---|---|---|
| Microbiological Examinations | | | | | |
| Microbial Enumeration Tests | Aerobic microbial count : Not more than 100 cfu/g | < 10 cfu/g | Not Performed | Not Performed | Not Performed |
| | Moulds and Yeasts : Not more than 10 cfu/g | < 10 cfu/g | Not Performed | Not Performed | Not Performed |
| Test for specified microorganisms | Salmonella species : Should be Absent/g | Not Detected | Not Performed | Not Performed | Not Performed |
| | Escherichia coli : Should be Absent/1g | Not Detected | Not Performed | Not Performed | Not Performed |
| Lab Notebook Reference / Page No. | | 19203B-8,21,32,36, 61, 138 | 19203B-115,128, 166,181 | 19203B-24,27, 40-41, 42-49, 175, 31-39, 60-113, 164-173 | 19203B-26-41, 70-83, |

NA = Not Applicable, ND = Not Detected, LOQ = Limit of Quantification, BQL = Below Quantification Limit
LOQ Limit: Chlordiazepoxide Related Compound A: 0.01%, Chlordiazepoxide: 0.01%, CPSP impurity: 0.01% & Impurity G: 0.01 %.
*Microbiological Examination result complied as per Nelson Labs Report No. # R-566468-R0

FIG. 7D

| Generic Name of Chlorthalidone Oral Suspension 5 mg/mL | | | Packing Details | | Bottle: 17 OZ Boston Round Shape PET Bottle, DAME CT (ALPHA PACK AGING, Printing No. GERALD-040449) CAP: 24 400 CRC AERI HP/TO Lined KEG O PETE PLASTICS, Drawing No.CGA-61156) |  |  |  |
|---|---|---|---|---|---|---|---|---|
| Batch No. | NH0910 | | | | | | | |
| Mfg. Date | | 02/2019 | Purpose of study | | Development Batch Stability Study | | | |
| Sterility Condition | 40±2 °C & RH 75% ± 5% | | API Details | | Chlorthalidone USP-EP Micronized, Batch No.: #BF500500A | | | |
| Shelf Life | 06/2019 | | API Manufacturer | | Erregierre (SpA) | | | |
| | | | | | Initial | 1 Month | 3 Month | 6 Month |
| Test | Specification | | | | Complies | Complies | Complies | Complies |
| Description | Yellow uniform suspension with strawberry flavor. | | | | Complies | Complies | Complies | Complies |
| Identification test (By HPLC) | The retention time of the major peak in the chromatogram of the Assay preparation corresponds to that of the internal standard, as obtained in the assay test. | | | | Complies | Complies | Complies | Complies |
| pH | Between 3.0 and 7.0 | | | | 5.32 | 4.65 | 4.28 | 4.01 |
| Specific Gravity | Between 1.0 to 1.3 | | | | 1.13 | 1.13 | 1.13 | 1.12 |
| Osmolarity (mOsm/kg) | For information only (*1:1 dilution with water) | | | | 1095 | 1138 | 1205 | 1115 |
| Dissolution (By HPLC) | Not less than 75% (Q) of labeled amount of Chlorthalidone is dissolves in 30 min. | | Minimum | | 81 % | 97 % | 93 % | 89 % |
| | | | Maximum | | 100 % | 103 % | 97 % | 96 % |
| | | | Mean | | 96 % | 101 % | 95 % | 93 % |
| Related Substance (By HPLC) | Chlorthalidone Related Compound A : Not more than 0.7 % | | | | 0.43% | 0.51% | 0.62% | Not Performed |
| | Impurity J : Not more than 0.2 % | | | | 0.01% | BQL | 0.01 % | Not Performed |
| | Impurity G : Not more than 0.3 % | | | | 0.11% | 0.09 % | 0.09 % | Not Performed |
| | CPSP : Not more than 0.10 % | | | | Not Detected | Not Detected | Not Detected | Not Performed |
| | Any individuals unknown impurity : Not more than 0.20 % | | | | 0.05 % | 0.03 % | 0.08 % | Not Performed |
| | Total impurities (Excluding Chlorthalidone Related Compound A) : Not more than 0.80 % | | | | 0.25% | 0.21 % | 0.35 % | Not Performed |
| Viscosity | 150 cps to 700 cps | | | | Not Performed | Not Performed | Not Performed | Not Performed |

FIG. 7E

| Generic Name: Chlorthalidone Oral Suspension 5 mg/mL | | | Bottle: 15 CC Brown Ronin Shape PET Bottle, 24-410 CT | | | | | |
|---|---|---|---|---|---|---|---|---|
| Batch No.: NCH19/13 | Package Details | | ALPHA PACKAGING, Drawing No.DHSA-P-241410 | | | | | |
| | | | CAP: 24-400 CRC ASSLY (WOV) Logo (ACCD. RTE) PK ALSTICK, Trimax ALS (LCOL 101-10) | | | | | |
| Mfg. Date: 12-2019 | Purpose of study | | Development Batch, Stability Study | | | | | |
| Storage Condition: 40°C ± 2°C at RH 75% ± 5% | API Details | | Chlorthalidone USP-EP Micronised, Batch No. # H1NH506A | | | | | |
| Study Started on: | API Manufacturer | | | | | | | |
| | | Bottom-1 | Bottom-2 | Middle-1 | Middle-2 | Top-1 | Top-2 | |
| Assay | | 100.4 | 100.3 | 100.4 | 100.3 | 99.7 | 99.5 | |
| | | 99.2 | 99.7 | 99.3 | 99.6 | 99.3 | 100.2 | |
| | | | | 1 Month | | | | |
| | | 98.5 | 99.2 | 98.1 | 98.9 | 98.3 | 98.3 | |
| | | | | 3 Month | | | | |
| | | 96.4 | 96.2 | 96.3 | 96.7 | 96.2 | 95.9 | |
| | | | | 6 Month | | | | |
| | | Bottom-1 | Bottom-2 | Middle-1 | Middle-2 | Top-1 | Top-2 | |
| Between 90.0% and 110.0% of labeled amount of Chlorthalidone | | 98.0 | 97.8 | 97.9 | 98.3 | 97.4 | 97.3 | |
| | | | | 1 Month | | | | |
| | | 98.3 | 98.8 | 98.5 | 98.7 | 99.1 | 99.3 | |
| | | | | 3 Month | | | | |
| | | 98.6 | 99.3 | 98.3 | 98.1 | 98.3 | 98.4 | |
| | | | | 6 Month | | | | |
| | | Bottom-1 | Bottom-2 | Middle-1 | Middle-2 | Top-1 | Top-2 | |
| Between 85.0% and 115.0% of labeled amount of Methyl Paraben | | 96.6 | 96.4 | 96.7 | 96.5 | 96.5 | 96.2 | |
| | | | | Initial | | | | |
| | | 96.9 | 96.8 | 96.9 | 97.1 | 96.4 | 96.4 | |
| | | | | 1 Month | | | | |
| | | 96.8 | 97.4 | 96.9 | 97.5 | 97.2 | 98.1 | |
| | | | | 3 Month | | | | |
| Between 85.0% and 115.0% of labeled amount of Propyl Paraben | | 96.8 | 97.6 | 96.6 | 97.4 | 96.5 | 96.6 | |
| | | | | 6 Month | | | | |
| | | 95.5 | 95.4 | 95.5 | 95.3 | 95.3 | 94.9 | |

FIG.7F

| | | Packing Details : | Bottle: 12 OZ Boston Round Shape PET Bottle, 24-410 CT ALPHA FACE, AGING, Drawing No. NEPRP 634A-03 CAP: 24-400 CRC ASSY PP/PE Liner SMOOTH RITE W/ACTIVE, Drawing No. KSS-10110 | | | |
|---|---|---|---|---|---|---|
| Generic Name : Chlorhexidine Oral Suspension 5 mg/mL | | | | | | |
| Batch No. : NC0319223 | | | | | | |
| Mfg. Date : 12-2019 | | Purpose of study : Development Batch, Stability Study | | | | |
| Storage Condition : 40 Cel. ± 2°C & RH 75% ± 5% | | API Details : Chlorhexidine USP-EP Micronized, Batch No. # BH9966XA | | | | |
| Study Started on : 12/26/2019 | | | | | | |
| Test | Specification | | Initial | 1 Month | 3 Month | 6 Month |
| *Microbiological Examination | | | | | | |
| Microbial Enumeration Tests | Aerobic microbial count : Not more than 100 cfu/g | | < 10 cfu/g | Not Performed | Not Performed | Not Performed |
| | Moulds and Yeasts : Not more than 10 cfu/g | | < 10 cfu/g | Not Performed | Not Performed | Not Performed |
| Test for specified microorganisms | Salmonella species : Should be Absent/g | | Not Detected | Not Performed | Not Performed | Not Performed |
| | Escherichia coli : Should be Absent/10g | | Not Detected | Not Performed | Not Performed | Not Performed |
| Lab Notebook Reference : Page No. | | | 192033-8, 21, 32, 86, 61, 128 | 192038-116, 128, 166, 181 | 192046-23-27, 40-41, 42-49, 33-38, 62-113, 164-174 | 192053-36-47, 70-83 |

NA = Not Applicable, ND = Not Detected, LOQ = Limit of Quantification, BQL = Below Quantification Limit
LOQ Limit: Chlorhexidine Related Compound A: 0.01%, Chlorhexidine: 0.01%, CPSP impurity: 0.01% & Impurity-G: 0.01 %.
*Microbiological Examination result complied as per Nelson Labs Report No. # R-566462-R0

CHLORTHALIDONE COMPOSITIONS AND METHODS

CROSS-REFERENCE DATA

This patent application claims a priority date benefit from the U.S. Provisional Patent Application No. 63/032,434 filed on 29 May 2020 with the same title.

FIELD OF THE INVENTION

The field of the invention is a liquid suspension of chlorthalidone, and especially a suspension of uniformly dispersed chlorthalidone.

BACKGROUND

The following description includes information that may be useful in understanding the present invention. It is not an admission that any of the information provided herein is prior art or relevant to the presently claimed invention, or that any publication specifically or implicitly referenced is prior art.

All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Chlorthalidone is a prescription diuretic drug used to treat high blood pressure (hypertension). Chlorthalidone is also used to reduce extra salt and water in the body caused by conditions such as heart failure, liver disease, and kidney disease, and is also used to treat diabetes. Currently, chlorthalidone is available as a prescription drug, and it is only manufactured as an oral tablet of 25 mg or 50 mg doses (Chlorthalidone Tablets USP, 25 mg and 50 mg).

Effective use and administration of a 25 mg or 50 mg Chlorthalidone tablet is prone to errors including miscalculated or imprecise doses. For example, an oral tablet formulation may need to be cut in half for administration of a prescribed dose amount; however accurately splitting the tablet can be problematic for some dosage amounts. Furthermore, while dosages which are multiples of 25 or 50 can be administered in oral tablet form, lower dosages (e.g., less than 25 mg) or dosages between 25 and 50 mg or higher than 50 mg and especially those which are not multiples of 25, are not easy to obtain from the 25 mg or 50 mg tablets.

Thus, there is still a need for an oral formulation of chlorthalidone for more precise and effective oral administration of the chlorthalidone at various dosage levels.

SUMMARY OF THE INVENTION

The inventive subject matter provides compositions and methods of a liquid suspension formulation of chlorthalidone. In particular, the contemplated composition is a stabilized chlorthalidone suspension including chlorthalidone at a concentration of between 1 to 20 mg/mL, a solubilizing agent and/or wetting agent, at least one suspending agent, at least one viscosity increasing agent or at least one anti-caking agent, and water.

Notably, despite the propensity of ingredients in suspension to settle, the dispersion of the chlorthalidone API presented herein remained substantially uniform throughout over extended periods, thus allowing for accurate dispensing and dosing. For example, a first sample concentration of the chlorthalidone in a first sample volume of the composition taken before storage differs from a second sample concentration in a second volume of the composition after storing for at least 3 hours, or even at least 6-12 hours by no more than 5%. More preferably, the first sample concentration of the chlorthalidone in the first sample volume of the composition taken before storage differs from the second sample concentration in the second sample volume of the composition after storage by no more than 2.5%. Most preferably, the first sample concentration of the chlorthalidone in the first sample volume of the composition taken after stirring to reach uniform dispersion and before storage differs from the second sample concentration in the second sample volume of the composition taken after storage by no more than 1.0%. Typically, the first sample volume is obtained from a section of the stabilized chlorthalidone suspension that is above or below and does not overlap in a vertical direction with the part of the stabilized chlorthalidone suspension from which the second sample volume is obtained.

In some embodiments, the stabilized chlorthalidone suspension includes chlorthalidone, a solubilizing or wetting agent, at least one suspending agent, at least one viscosity increasing agent or at least one anti-caking agent, water, and further includes an anti-foaming agent, at least one antimicrobial, and at least one sweetening agent.

Preferably, the chlorthalidone is present in the stabilized suspension at a concentration of 1 to 20 mg/mL. More preferably, the chlorthalidone is present in the stabilized suspension at or between about 5 to 15 mg/mL. Most preferably, the chlorthalidone is present in the stabilized suspension at about 10 mg/mL.

The solubilizing or wetting agent in the stabilized suspension may be any suitable poloxamer, which is a wetting (e.g., emulsifying) agent. Preferably, the wetting agent is poloxamer 188, poloxamer 124, or poloxamer 237. Typically, the wetting agent is poloxamer 188. More typically, the wetting agent is poloxamer 188 at a concentration at or between 5 to 20 mg/mL. Most typically, the wetting agent is poloxamer 188 at a concentration of about 10 mg/mL.

The suspending agent in the stabilized suspension may be a polysaccharide suspending agent and/or a synthetic suspending agent. In preferred embodiments, the suspending agent is one or more polysaccharide suspending agent selected from microcrystalline cellulose (MCC), acacia gum, tragacanth gum, xantham gums, starch, or alginates. More preferably, the polysaccharide suspending agent is MCC. Typically, the MCC is present in the stabilized suspension at a concentration of between about 10 to 20 mg/mL. More typically, the MCC is present in the stabilized suspension at a concentration of 20 mg/mL.

The viscosity increasing agent and/or anti-caking agent in the stabilized suspension may be selected from hydroxyethylcellulose (HEC), silicon dioxide, and/or polyethylene glycol (PEG). Notably, a suitable viscosity increasing agent may also be an anti-caking agent. Typically, the viscosity agent or anti-caking agent is present in the stabilized suspension at or between 0.1% to 5% by weight (wt %). Preferably, viscosity increasing agent and/or anti-caking agent in the stabilized suspension includes HEC and silicon dioxide. In preferred embodiments, the HEC (for HEC having a viscosity of 400 centipoise (cps)) is present in the stabilized suspension at a concentration at or between about 1 to 30 mg/mL or at or between 1 to 5 mg/mL, and the silicon dioxide (alone or together with the HEC) is present in the stabilized suspension at a concentration at or between about 10 to 45 mg/mL or 15 to 25 mg/mL. In more preferred embodiments, in addition to HEC and silicon dioxide, polyethyleneglycol (PEG) is included in the stabilized suspension at or between about 25 and 50 mg/mL. The PEG may have a molecular weight at or between 300 to 1,000 gram/mol (g/mol). For HEC having a viscosity of 2,000 cps, an amount from about 0.25 to 1.25 mg/mL HEC is added to the stabilized suspension. More preferably, the amount of HEC (at 2,000 cps) is about 0.25 mg/mL. In some embodiments, the stabilized chlorthalidone suspension also includes a flavor, a flavoring agent, a coloring agent, and/or a dye.

The inventive subject matter includes methods for making the contemplated stabilized chlorthalidone suspension. A contemplated method includes preparing the suspension using water. Typically, the method includes adding to water: a solubilizing and/or a wetting agent with stirring, adding a suspending agent with stirring and homogenizing, adding at least one viscosity increasing agent and/or at least one caking agent with stirring and homogenizing, and adding a solubilized solution of chlorthalidone with stirring and homogenizing.

In preferred embodiments, a contemplated method for making the stabilized chlorthalidone suspension includes making a first mixture by adding a solubilizing and/or a wetting agent to a first volume of water having a temperature of between about 25° C. to 30° C. with stirring, adding a suspending agent to the first volume of water with stirring and homogenizing, and adding at least one viscosity increasing agent or at least one anti-caking agent to the first volume of water with stirring and homogenizing. The contemplated method also includes making a second mixture by adding a sweetening agent to a second volume of water with stirring, adding a viscosity increasing agent to the second volume of water with stirring, and adding chlorthalidone at between about 5 to 20 mg/mL to the second volume of water with stirring and homogenizing. The stabilized chlorthalidone suspension is formed by combining the first mixture and the second mixture with stirring to form a third mixture and homogenizing. In some embodiments, additional water may be added to bring the mixture to the calculated volume for the desired concentration of components including chlorthalidone.

In typical embodiments of any of the methods disclosed above or any method set forth below, the solubilizing and/or a wetting agent may be one of poloxamer 188, poloxamer 124, or poloxamer 237. In more typical embodiments, the solubilizing and/or a wetting agent is poloxamer 188. Preferably, the poloxamer 188 is added to the water or the first volume of water to have a final concentration of between about 5 mg/mL to about 20 mg/mL. Most preferably, the final concentration of the poloxamer 188 is 10 mg/mL.

In further typical embodiments of the method disclosed above or any method set forth below, the suspending agent is a polysaccharide suspending agent and/or a synthetic suspending agent. Examples of a polysaccharide suspending agent include microcrystalline cellulose (MCC), acacia gum, tragacanth gum, xantham gums, starch, or alginates. Preferably, the suspending agent is MCC added to the water or the first volume of water to have a final concentration of between about 10 to 20 mg/mL. Most preferably, the final concentration of the MCC added to the water or the first volume of water is about 20 mg/mL.

In still further typical embodiments of the method disclosed above or any method set forth below, the at least one viscosity increasing agent or the at least one anti-caking agent is hydroxyethylcellulose and/or silicon dioxide. Preferably, the at least one viscosity increasing agent or the at least one anti-caking agent is added to the water or the first volume of water to have a final concentration of between about 0.1 to 5% by weight (wt %).

In more preferred embodiments, the contemplated method for making the stabilized chlorthalidone suspension includes making the first mixture as disclosed above, wherein making the first mixture further includes heating the water to about 80° C. to 85° C., adding at least one antimicrobial preservative to the heated water with stirring, and ambiently cooling the water to about 25° C. to 30° C., all of which occur prior to adding the solubilizing and/or a wetting agent. Preferably, the at least one antimicrobial is methyl paraben, propyl paraben, and/or potassium sorbate.

In additional preferred embodiments, making the first mixture further includes adding an anti-foaming agent to the first volume of water with stirring. Preferably the anti-foaming agent is simethicone. In other preferred embodiments, making the first mixture further includes adding a sweetening agent with stirring and homogenizing. Typically, the sweetening agent is sucrose, sucralose, glycerin, stevia, and/or sorbitol.

In still other embodiments, the contemplated stabilized chlorthalidone suspension includes chlorthalidone at a concentration of between 1 to 20 mg/mL, a solubilizing and/or a wetting agent, at least one suspending agent, at least two viscosity increasing agents, water, an anti-foaming agent, at least one antimicrobial, a buffering agent, and at least one sweetening agent, wherein a first concentration of the chlorthalidone in a first volume of the composition differs from a second concentration in a second volume of the composition by 1% or less.

With reference to the above stabilized chlorthalidone suspension, in preferred embodiments, the chlorthalidone is at a concentration of 5 mg/mL or 10 mg/mL, the solubilizing and/or a wetting agent is propylene glycol (PPG), the at least one suspending agent is microcrystalline cellulose (MCC), the at least two viscosity increasing agents are selected from hydroxyethylcellulose (HEC), xanthan gum, and glycerin, the water is deionized water, the anti-foaming agent is simethicone, the buffering agent is citric acid anhydrous, and the sweetening agent is sucralose.

In related embodiments, a method for making the above stabilized chlorthalidone suspension includes forming a first mixture including heating a first volume of water and a first solubilizing agent to 80° C. to 85° C., wherein the first volume of water is 40% to 60% of the volume of the stabilized chlorthalidone suspension and the solubilizing agent is 0.5%. The first mixture also includes adding at least one anti-microbial/preservative to the first mixture with stirring at 80° C. to 85° C., cooling the first mixture without applying an external source to 25° C. to 30° C., adding an anti-foaming agent to the first mixture with homogenization, wherein the anti-foaming agent is added at 50 to 75% of the concentration of the anti-foaming agent in the stabilized chlorthalidone suspension. The first mixture also includes adding a suspending agent and a sweetening agent to the first mixture either sequentially or simultaneously with stirring and/or homogenization, adding an anti-caking agent to the first mixture with stirring and/or homogenization, adding a first viscosity increasing agent to the first mixture with stirring, and adding a second viscosity increasing agent to the first mixture with stirring.

The method for making the above stabilized chlorthalidone suspension also includes forming a second mixture including adding 50 to 25% of the concentration of the anti-foaming agent in the stabilized chlorthalidone suspension to a second volume of water with stirring, wherein the second volume of water is 40 to 60% of the volume of the stabilized chlorthalidone suspension, adding a second solubilizing and/or a second wetting agent to the second mixture with stirring, and adding chlorthalidone to the second mixture with stirring.

The method for making the above stabilized chlorthalidone suspension also includes forming a third mixture including mixing the first mixture and the second mixture with stirring, and adding a buffering agent and optionally a flavor to the third mixture with stirring.

With reference to the above method for making the stabilized chlorthalidone suspension, in preferred embodiments, the method includes the first solubilizing and/or a wetting agent is polypropylene glycol (PPG), the at least one anti-microbial/preservative is methyl paraben, poly paraben, and/or potassium sorbate, the anti-foaming agent is simethicone, the suspending agent is microcrystalline cellulose (MCC), the anti-caking agent is hydroxyethylcellulose (HEC), the first viscosity increasing agent is xanthan gum, the second viscosity increasing agent is glycerin, the second solubilizing and/or a wetting agent is poloxamer 188, and the buffering agents.

In still other preferred embodiments, any of the above methods for making a stabilized chlorthalidone suspension include adding a flavor, a flavoring agent, a coloring agent, and/or a dye the water, or one of the first mixture, the second mixture, or the third mixture with stirring.

Preferably, the contemplated methods of making a stabilized chlorthalidone suspension render a suspension wherein a first concentration of the chlorthalidone in a first volume of the stabilized chlorthalidone differs from a second concentration in a second volume of the composition by 2.5% or less. More preferably, the first concentration of the chlorthalidone in a first volume of the stabilized chlorthalidone differs from a second concentration in a second volume of the composition by 1.0% or less.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIG. 1C is a flow chart depicting exemplary method steps of Process A, for mixing the first mixture of FIG. 1A and the second mixture of FIG. 1B, according to embodiments of the present invention.

FIG. 1F is a flow chart depicting exemplary method steps of Process B, for mixing the first mixture of FIG. 1D and the second mixture of FIG. 1E, according to embodiments of the present invention.

FIGS. 3A-3K are tables showing exemplary variations in the formulations of the dispersed chlorthalidone suspension, according to embodiments of the present invention.

FIGS. 4A-4F are tables showing exemplary stability data for batch NCH1972 at 25° C. (FIGS. 4A-4C) and 40° C. (FIGS. 4D-4F), according to embodiments of the present invention.

FIGS. 5A-5F are tables showing exemplary stability data for batch NCH1979 at 25° C. (FIGS. 5A-5C) and 40° C. (FIGS. 5D-5F), according to embodiments of the present invention.

FIGS. 6A-6F are tables showing exemplary stability data for batch NCH1984 at 25° C. (FIGS. 6A-6C) and 40° C. (FIGS. 6D-6F), according to embodiments of the present invention.

FIGS. 7A-7F are tables showing exemplary stability data for batch NCH19122 at 25° C. (FIGS. 7A-7C) and 40° C. (FIGS. 7D-7F), according to embodiments of the present invention.

DETAILED DESCRIPTION

Figure 1A:
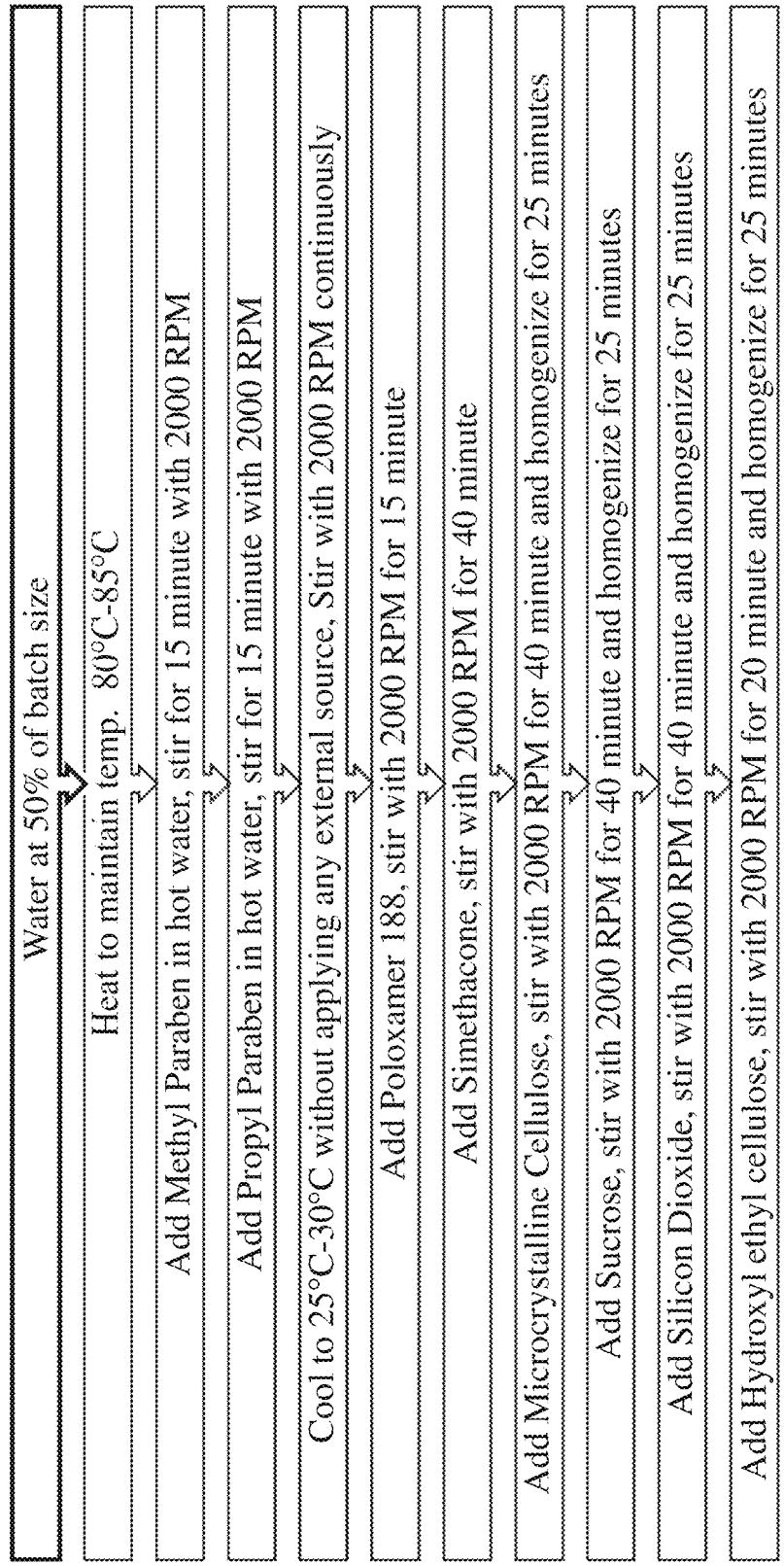
FIG. 1A is a flow chart depicting exemplary method steps for preparing a first mixture (Mixture 1) of Process A, according to an embodiment of the present invention.

The inventors have discovered compositions and methods for a chlorthalidone suspension for oral administration. In particular, the suspensions according to the inventive subject matter provide an unexpected stable dispersion of chlorthalidone in a liquid formulation. For example, the stably dispersed chlorthalidone suspension is characterized by having a remarkably low settling rate, rendering a liquid formulation having the chlorthalidone active ingredient uniformly dispersed at the same concentration or approximately the same concentration throughout the suspension such that any sample of the suspension taken corresponds to the same or approximately the same concentration of another sample taken, even after extended periods of time. Accordingly, one should appreciate that the disclosed stabilized suspensions of chlorthalidone provide a chlorthalidone formulation that is easily and accurately dosed during manufacture as well as use with a patient.

In particular, the contemplated composition is a stabilized chlorthalidone suspension including chlorthalidone as the active pharmaceutical ingredient (API) at a concentration of between 1 to 20 mg/mL, with excipients including at least a solubilizing and/or a wetting agent, at least one suspending agent, at least one viscosity increasing agent or at least one anti-caking agent, and water. Preferably, the presently disclosed composition and methods provide for a chlorthalidone suspension having a first concentration of the chlorthalidone in a first volume of the composition that differs from a second concentration in a second volume of the composition by no more than 5%. In other words, the chlorthalidone suspension is at least 95% homogenous with respect to the concentration of chlorthalidone found throughout the dispersion. Preferably, the chlorthalidone suspension is at least 95% homogenous with respect to all components. As disclosed herein, the first concentration of the suspension may differ from the second concentration by no more than 0.5%. Accordingly, the contemplated chlorthalidone suspension may have a first concentration of chlorthalidone in a first volume of the composition that differs from a second concentration in a second volume of the composition by no more than 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.5%, 3.6%, 3.7%, 3.8%, 3.9%, 4.0%, 4.1%, 4.2%, 4.3%, 4.4%, 4.5%, 4.6%, 4.7%, 4.7%, 4.9%, or 5.0%.

In some embodiments, it is contemplated that the suspension maintains uniform concentration over extended storage times. For example, the chlorthalidone formulations presented herein may be stored over a time period of at least 20 min, at least 30 min, at least 40 min, at least 50 min, at least 1 hr, at least 2 hrs, at least 3 hrs, at least 4 hrs, at least 5 hrs, at least 6 hrs, at least 9 hrs, at least 12 hrs, at least 18 hrs, at least 24 hrs, at least 36 hrs, at least 48 hrs, at least 72 hrs, at least 4 days, at least 5 days, at least 6 days, at least 7 days, at least 10 days, at least 20 days, at least 30 days, at least 45 days, at least 2 months, at least 3 months, at least 4 months, at least 5 months, or at least 6 months. During such time period, it is contemplated that after initial stirring to generate a homogenous suspension, the chlorthalidone in a first sample taken from the composition immediately after stirring will differ from a second sample in a second volume of the composition by no more than 10%, or no more than 9%, or no more than 8%, or no more than 7%, or no more than 6%, or no more than 5%, or no more than 4%, or no more than 3%, or even less. Advantageously, such stable suspensions will not only ensure uniform drug concentration during dispensing from a large holding tank to individual use containers in a production environment, but also help maintain uniform drug concentration at the point of use to so ensure proper individual dosing of the drug. In further examples, a second sample of suspension for detecting of the chlorthalidone concentration is contemplated to be taken after a period of composition storage time of at least 10 min after taking the first sample from which the chlorthalidone concentration is determined.

Preferably, the chlorthalidone is present in the stabilized suspension at a concentration of 1 to 20 mg/mL. More preferably, the chlorthalidone is present in the stabilized suspension at or between about 5 to 15 mg/mL. Most preferably, the chlorthalidone is present in the stabilized suspension at about 5 mg/mL or 10 mg/mL.

Notably, initial experiments revealed an expected outcome, in that the chlorthalidone API was not stable in solution as it would agglomerate and cake. Accordingly, for stabilizing the chlorthalidone in a stabilized suspension, the inventors contemplated combining the chlorthalidone with select excipients. These excipients include at least a solubilizing and/or a wetting agent, at least one suspending agent, at least one viscosity increasing agent or at least one anti-caking agent, and water. The suspension may also further include an anti-foaming agent, at least one antimicrobial, and at least one sweetening agent.

Unless disclosed otherwise, the contemplated suspension may include any excipient disclosed herein at a final concentration of no more than its inactive ingredient (IIG) limit as set by the U.S. Food and Drug Administration (FDA) for that excipient compound. For example, as set forth in Tables 1A and 1B below, exemplary excipients are listed along with the corresponding JIG limit, function, and concentration (e.g., final concentration) in each of the 10 mg/mL chlorthalidone suspension including Formulation 1 (NCH1972), Formulation 2 (NCH1979), and Formulation 3 (NCH1984) of Process A and the excipients added to a 5 mg/mL chlorthalidone suspension prepared according to Process B, as disclosed herein below.

The solubilizing and/or a wetting agent in the stabilized chlorthalidone suspension may be any suitable poloxamer (a wetting agent). For example, the wetting agent may be poloxamer 188, poloxamer 124, or poloxamer 237. As used herein, the wetting agent is poloxamer 188. Poloxamer 188 may be used at a final concentration at or between about 5 to 20 mg/mL. Preferably, poloxamer 188 is present in the stabilized suspension at a concentration of about 10 mg/mL.

The suspending agent in the stabilized chlorthalidone suspension may be any suitable suspending agent. In general, suspending agents include polysaccharide suspending agents, synthetic suspending agent, and salts. However, salt suspending agents are not suitable for use with chlorthalidone as salt is known to increase hypertension and therefore would be counterproductive for the intended treatment. Accordingly, suspending agents for the contemplated chlorthalidone suspension include polysaccharide suspending agents and synthetic suspending agents. Preferably, the polysaccharide or synthetic suspending agents are not charged at the pH of the chlorthalidone suspension which may have a pH of between 3.0 and 7.0. Typically, the pH of the chlorthalidone suspension is of between 4.0 and 6.0, and more typically the pH of the chlorthalidone suspension is of between 4.5 and 5.5. For example, polysaccharide suspending agents include one or more of microcrystalline cellulose (MCC), acacia gum, tragacanth gum, xanthan gums, starch, and/or alginates. For example, a polysaccharide suspending agent may be MCC and xanthan gum. In another example, the polysaccharide suspending agent is MCC. Typically, the MCC or MCC and xanthan gum are present in the stabilized suspension at a total concentration of between about 10 to 20 mg/mL. More typically, the MCC or MCC and xanthan gum are present in the stabilized suspension at a total concentration of about 20 mg/mL.

The viscosity increasing agent and/or anti-caking agent includes any suitable compound that increases viscosity and/or decreases caking. Notably, a suitable viscosity increasing agent may also be an anti-caking agent. The viscosity increasing agent and/or anti-caking agent in the stabilized suspension may be hydroxyethylcellulose (HEC), silicon dioxide, and/or polyethylene glycol (PEG). Typically, the viscosity agent or anti-caking agent is present in the stabilized suspension at or between 0.1% to 5% by weight (wt %). Preferably, viscosity increasing agent and/or anti-caking agent in the stabilized suspension includes HEC and/or silicon dioxide. In preferred embodiments, the HEC is present in the stabilized suspension at a concentration at or between about 0.25 to 1.25 mg/mL for HEC with a viscosity of 2,000 centipoise (cps) or at about 1 to 30 mg/mL for HEC with a viscosity of 400 cps. The silicon dioxide (alone or together with the HEC) is present in the stabilized suspension at a concentration at or between about 10 to 70 mg/mL, about 10 to 45 mg/mL, or about 15 to 25 mg/mL. In more preferred embodiments, in addition to HEC and silicon dioxide, polyethylglycol (PEG) is included in the stabilized suspension at or between about 25 and 50 mg/mL. The PEG may have a molecular weight at or between 300 to 1,000 gram/mol (g/mol).

To enable more thorough mixing during production, the chlorthalidone suspension may also include an anti-foaming agent. Any suitable anti-foaming agent may used. Suitable anti-foaming agents include silicon-based (e.g., simethicone (simeticone), silicone, or polydimethylsiloxane), food grade mineral oils (e.g., mono- and diglycerides), or alginates (e.g., alginic acid). Preferably, the anti-foaming agent is simethicone (also referred to as simeticone). More preferably, simethicone is present in the stabilized suspension at a concentration of between about 5 mg/mL to about 9 mg/mL. Most preferably, simethicone is present at a concentration between about 8 mg/mL to about 9 mg/mL.

To prevent contamination and microbial growth in the stabilized chlorthalidone suspension, any suitable antimicrobial agent may be provided. Suitable antimicrobial compounds include one or more of methyl paraben, propyl paraben, and potassium sorbate (K-sorbate). Preferably, both methyl paraben and propyl paraben and/or potassium sorbate are present in the suspension. For example, methyl paraben may be present in the stabilized suspension at a concentration of between about 1 to 200 mg/mL, and propyl paraben may be present in the stabilized suspension at a concentration of between about 0.1 up to 40 mg/mL. Preferably, if both methyl paraben and propyl paraben are present in the suspension, an exemplary concentration of methyl paraben is about 1 mg/mL and an exemplary concentration of propyl paraben is about 0.2 mg/mL. Exemplary concentrations of potassium sorbate are of between about 1 to 5 mg/mL.

Additionally, sweetening agents may be added to the stabilized chlorthalidone suspension to mask unpleasant tastes or odors and facilitate consumption of the suspension by the subject (e.g., person or animal) in need of chlorthalidone. Accordingly, any suitable sweetening agent may be added to the stabilized suspension. Exemplary sweetening agents include sorbitol, sucrose, sucralose, stevia, and/or glycerin. Preferably, the concentration of sorbitol present in the stabilized suspension is of between about 50 mg/mL up to 975 mg/mL of a 70% sorbitol solution. More preferably, the concentration of sorbitol present in the stabilized suspension is about 200 mg/mL up to about 500 mg/mL, or about 300 mg/mL. Preferably, the concentration of sucrose present in the stabilizes suspension is of between about 50 mg/mL up to 500 mg/mL. More preferably, the concentration of sucrose is present in the stabilized suspension is about 100 mg/mL up to about 300 mg/mL, or about 150 mg/mL. Typically, sorbitol and sucrose are both present in the stabilized suspension. In other preferred embodiments, for diabetic patients in need of chlorthalidone, sucralose or stevia may be present with glycerin in the stabilized suspension.

While the color and flavor of a liquid formulation for oral administration does not affect the stability of an API and excipients in a suspension, both color and flavor may further help the subject in need of chlorthalidone consume the suspension more readily and/or with less stress. Accordingly, any food grade flavor or color agent may be included in the stabilized chlorthalidone suspension. Non-limiting examples of flavors include fruit flavors (e.g., strawberry, orange, grape, or cherry). Non-limiting examples of colors or dyes, include yellow, red, and blue, and all reasonable combinations thereof.

Advantageously, the inventors have contemplated a method for producing a stabilized chlorthalidone suspension having a thoroughly dispersed concentration of chlorthalidone such that any two sample volumes of the suspension have a concentration of chlorthalidone that differs from the other by no more than about 5%, and preferably no more than about 1%. Typically, a first sample volume is obtained from a section of the stabilized chlorthalidone suspension that is above or below and does not overlap in a vertical direction with the section of the stabilized chlorthalidone suspension from which a second sample volume is obtained. For example, the first sample volume may be obtained from the bottom section of the stabilized chlorthalidone suspension with the second sample volume being obtained from the top section of the stabilized chlorthalidone suspension, and the concentration of chlorthalidone in each of the two sample volumes does not differ by more than 5%, thereby indicating that the chlorthalidone is homogenously dispersed in the suspension and does not readily settle after an initial mixing (e.g., shaking). Such a thorough dispersion has minimal or no lumps or caking. Accordingly, the contemplated method for making the stabilized chlorthalidone suspension includes preparing the suspension using water and adding to the water: a solubilizing and/or a wetting agent with stirring, adding a suspending agent with stirring and homogenizing, adding at least one viscosity increasing agent and/or at least one caking agent with stirring and homogenizing, and adding a solubilized solution of chlorthalidone with stirring and homogenizing.

Figure 1B:
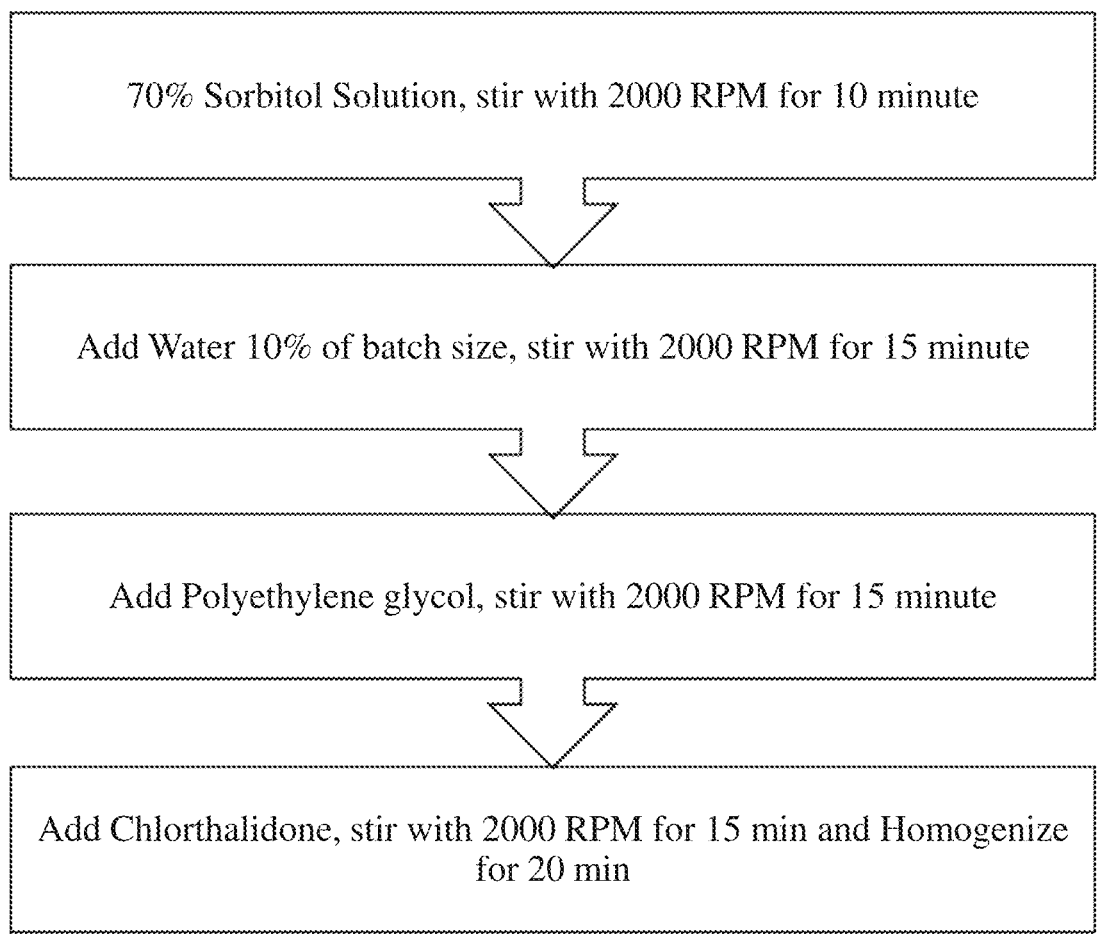
FIG. 1B is a flow chart depicting exemplary method steps for preparing a second mixture (Mixture 2) of Process A, according to embodiments of the present invention.

With reference to FIGS. 1A, 1B, and 1C, a preferred method (Process A) for making a stabilized chlorthalidone suspension includes making a first mixture by adding a solubilizing and/or a wetting agent to a first volume of water having a temperature of between about 25° C. to 30° C. with stirring, adding a suspending agent to the first volume of water with stirring and homogenizing, and adding at least one viscosity increasing agent or at least one anti-caking agent to the first volume of water with stirring and homogenizing. The first volume of water may be at or between 30% to 60% of the total end volume of the stabilized chlorthalidone suspension. For example, the first volume of water may be 30, 35, 40, 41, 42, 43, 44, 45, 46, 47, 48, 49 50, 51, 52, 52, 53, 54, 55, or 60% of the total volume (total batch volume) of the suspension.

The contemplated method also includes making a second mixture by adding a sweetening agent to a second volume of water with stirring, adding a viscosity increasing agent to the second volume of water with stirring, and adding chlorthalidone at between about 5 to 20 mg/mL to the second volume of water with stirring and homogenizing. The stabilized chlorthalidone suspension is formed by combining the first mixture and the second mixture with stirring to form a third mixture and homogenizing. In some embodiments, additional water may be added to bring the mixture to the calculated volume for the desired concentration of components including chlorthalidone.

In typical embodiments of any of the methods disclosed above or any method set forth below, the solubilizing and/or a wetting agent may be a wetting agent selected as one of poloxamer 188, poloxamer 124, or poloxamer 237. In more typical embodiments, the wetting agent is poloxamer 188. Preferably, the poloxamer 188 is added to the water or the first volume of water to have a final concentration of between about 5 mg/mL to about 20 mg/mL. Most preferably, the final concentration of the poloxamer 188 is 10 mg/mL.

In typical embodiments of any of the methods disclosed herein, the suspending agent is a polysaccharide suspending agent and/or a synthetic suspending agent. Examples of a polysaccharide suspending agent include microcrystalline cellulose (MCC), acacia gum, tragacanth gum, xantham gums, starch, and/or alginates. Preferably, the suspending agent is MCC or MCC and xantham gum added to the water or the first volume of water at a final concentration of between about 10 to 20 mg/mL. Most preferably, the final concentration of the MCC or MCC and xantham gum are added to the water or the first volume of water is about 20 mg/mL.

In typical embodiments of any of the methods disclosed herein, the at least one viscosity increasing agent or the at least one anti-caking agent is hydroxyethylcellulose and/or silicon dioxide. Preferably, the at least one viscosity increasing agent or the at least one anti-caking agent is added to the water or the first volume of water to have a final concentration of between about 0.1 to 5% by weight (wt %).

In more preferred embodiments, the contemplated method for making the stabilized chlorthalidone suspension includes making the first mixture as disclosed above, wherein making the first mixture further includes first heating the water to about 80° C. to 85° C., adding at least one antimicrobial preservative to the heated water with stirring, and ambiently cooling the water to about 25° C. to 30° C., all of which occur prior to adding the solubilizing and/or the wetting agent. Preferably, the at least one antimicrobial is methyl paraben and/or propyl paraben. More preferably, the at least one antimicrobial is both methyl paraben and propyl paraben.

In additional preferred embodiments, making the first mixture further includes adding an anti-foaming agent to the first volume of water with stirring. Preferably the anti-foaming agent is simethicone. In other preferred embodiments, making the first mixture further includes adding a sweetening agent with stirring and homogenizing. Typically, the sweetening agent is sucrose, sucralose, stevia, and/or glycerin. Preferably, the sweetening agent is sucralose which is an acceptable sweetener for diabetics.

In still other preferred embodiments, the contemplated method of making a stabilized chlorthalidone suspension includes adding a flavor, a flavoring agent, a coloring agent, and/or a dye the water, or one of the first mixture, the second mixture, or the third mixture with stirring.

Preferably, the contemplated method of making a stabilized chlorthalidone suspension renders a suspension wherein a first concentration of the chlorthalidone in a first volume of the stabilized chlorthalidone differs from a second concentration in a second volume of the composition by 2.5% or less. More preferably, the first concentration of the chlorthalidone in a first volume of the stabilized chlorthalidone differs from a second concentration in a second volume of the composition by 1.0% or less.

Figure 1D:
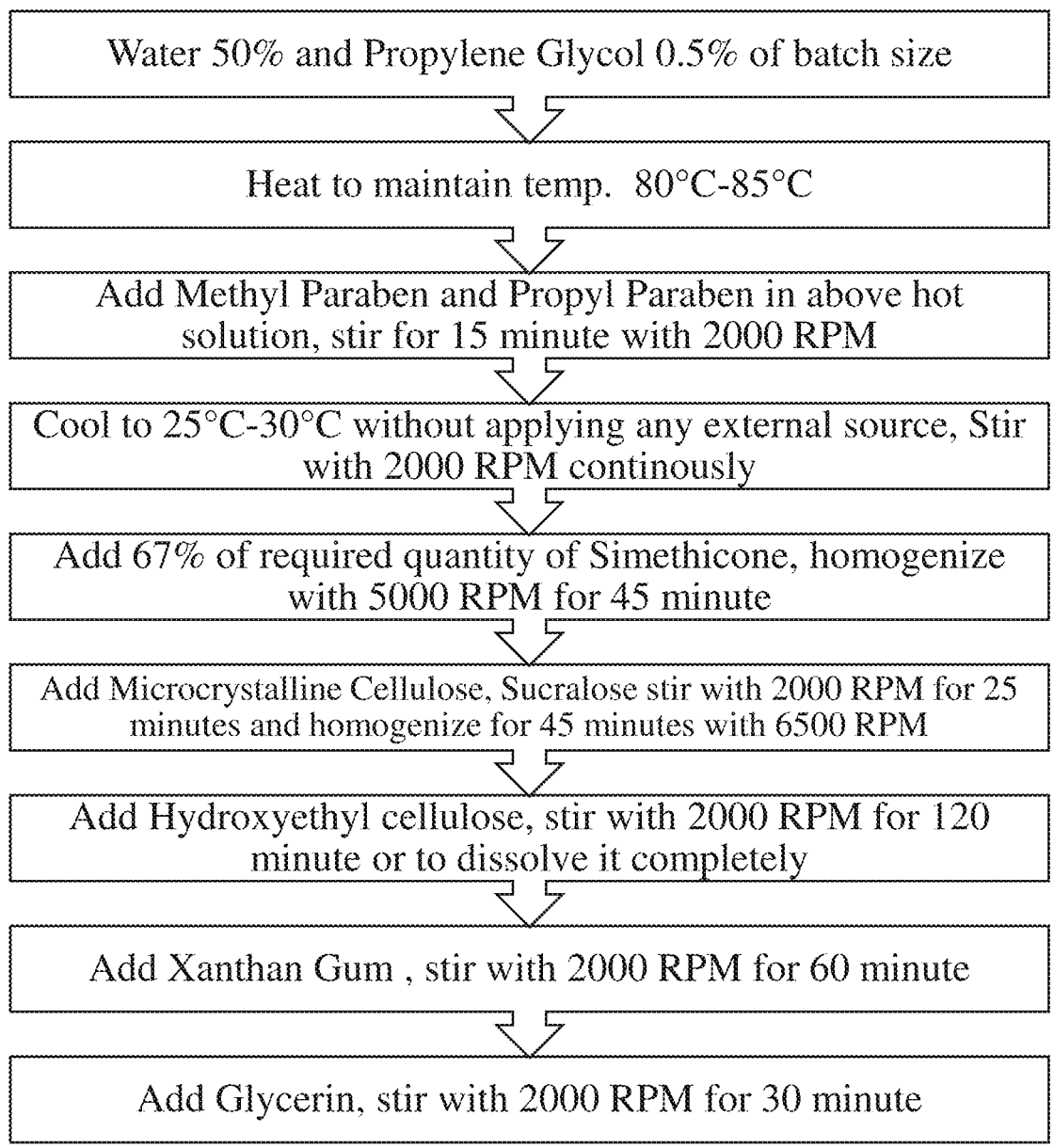
FIG. 1D is a flow chart depicting exemplary method steps for preparing a first mixture (Mixture 1) of Process B, according to embodiments of the present invention.
Figure 1E:
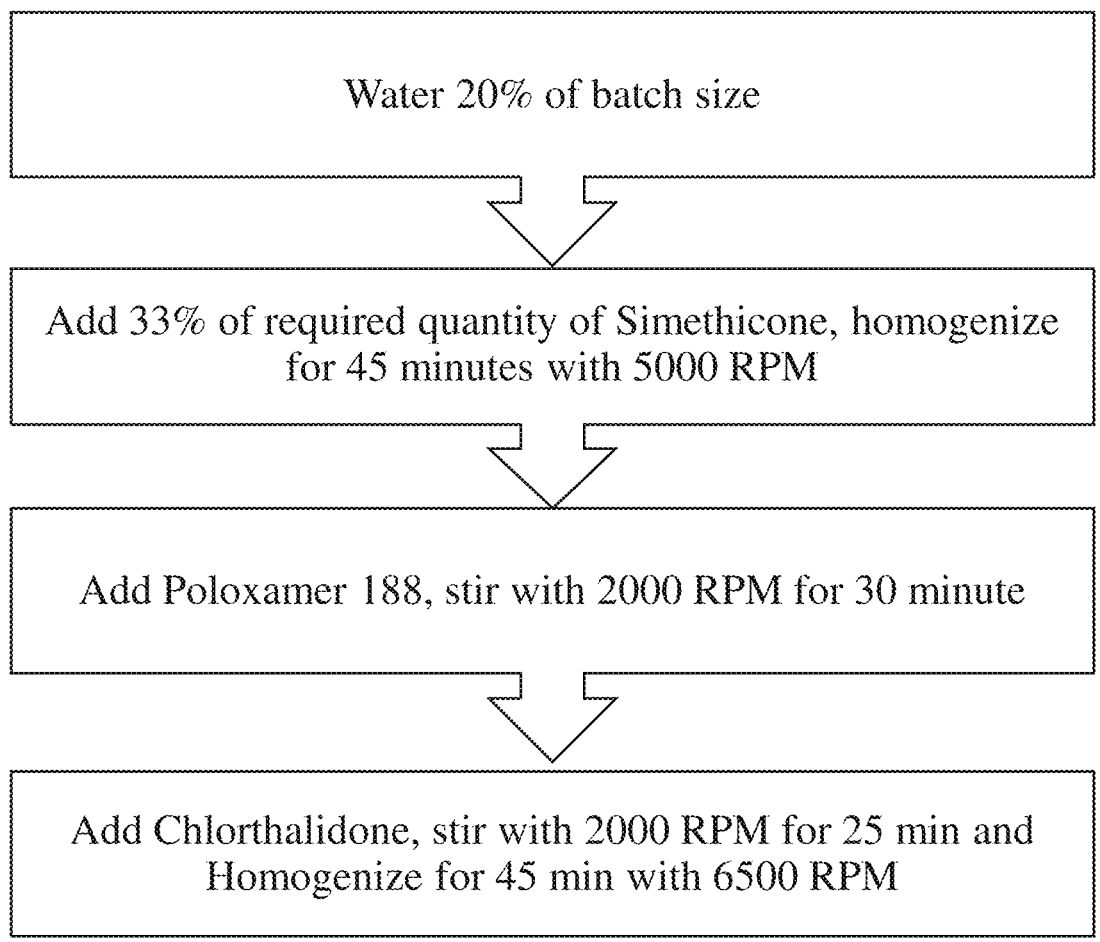
FIG. 1E is a flow chart depicting exemplary method steps for preparing a second mixture (Mixture 2) of Process B, according to embodiments of the present invention.
Figure 2:
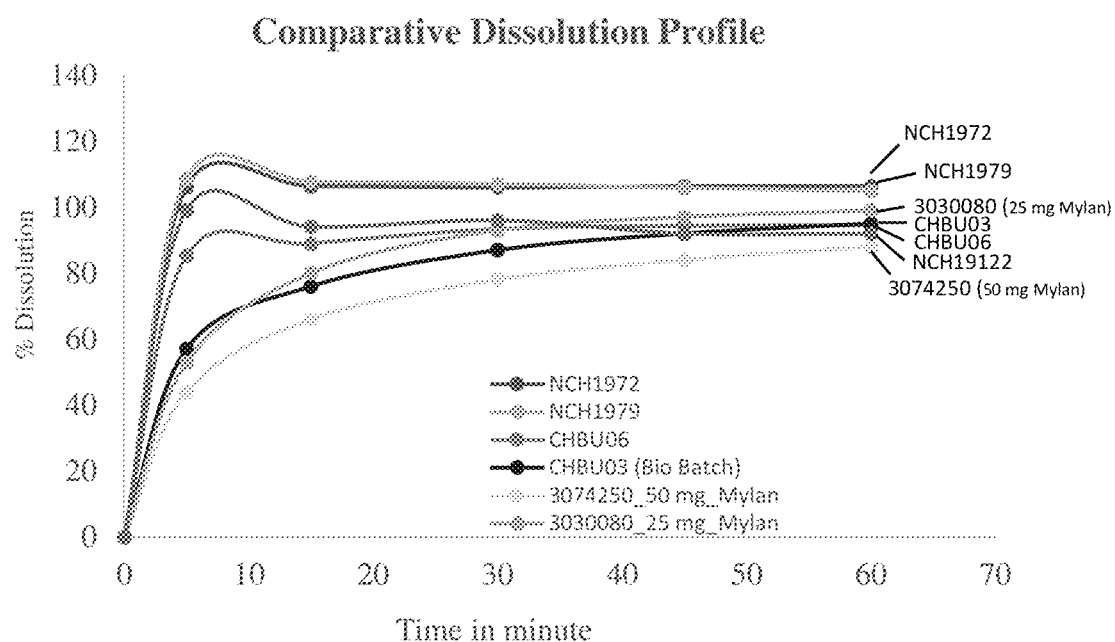
FIG. 2 is a graph of exemplary chlorthalidone suspensions as indicated, as disclosed herein and prepared according to embodiments of the present invention.

With reference to FIGS. 1D, 1E, and 1F, a preferred method (Process B) for making a stabilized chlorthalidone suspension includes Steps I, II, and III. While Step I is described first, it would be understood that the solution mixture of Step II could be prepared first and then added to the solution mixture of Step I, or vice versa.

With reference to FIG. 1D (Step I of Process B), a method for making a stabilized chlorthalidone suspension includes a preparing a first solution mixture by adding a solubilizing and/or a wetting agent to a first volume of water having a temperature of between about 80° C. to 85° C. Preferably, the first volume of water is about 40% to 60% of the total batch volume of the final suspension, and more preferably, the first volume of water is 50% of the total batch volume of the final suspension. A solubilizing and/or a wetting agent is added to the first volume of water having a temperature of between about 80° C. to 85° C. Preferably, the solubilizing and/or the wetting agent is propylene glycol (PPG)(density of 1.04 g/ml). Typically, the amount of PPG is of or between about 0.20% to 1.0% of the total volume of the stabilized chlorthalidone suspension. More typically, the amount of PPG is of or between about 0.40% to 0.60% of the total volume of the stabilized chlorthalidone suspension. Most preferably, the amount of PPG is of or about 0.50% the total volume of the stabilized chlorthalidone suspension. In exemplary embodiments, the weight amount of PPG for a 5 mg/mL stabilized chlorthalidone suspension is 4.5 to 5.5 mg/mL. In more preferred embodiments, a 5 mg/mL stabilized chlorthalidone suspension includes PPG at 5.2 mg/mL.

With continued reference to FIG. 1D, a preservative is added to the heated water with PPG. Typically, the preservative is at least one of methyl paraben and propyl paraben, and more typically, both methyl paraben and propyl paraben are added. In the presence of PPG, the addition of both methyl paraben and propyl paraben may be sequential (e.g., one added immediately after the other), or each may be added simultaneously, and stirred. For sufficient mixing, the stirring may occur at 1,500 to 2,500 RPM for 10 to 15 minutes. Most preferably, the stirring occurs at 2,000 RPMS for 15 minutes. Methyl paraben may be present in the stabilized suspension at a concentration of between about 1 to 200 mg/mL, and propyl paraben may be present in the stabilized suspension at a concentration of between about 0.1 up to 40 mg/mL. Preferably, if both methyl paraben and propyl paraben are present in the suspension, an exemplary concentration of methyl paraben is about 1 mg/mL and an exemplary concentration of propyl paraben is about 0.2 mg/mL.

With continued reference to FIG. 1D, after the addition of a preservative (e.g., methyl paraben and/or propyl paraben) to the heated water and PPG solution, the solution is allowed to cool to 25° C. to 30° C. with removal of heat, and without applying any external source. Typically, stirring (e.g., at or between 1,500 to 2,500 RPM) continues during the cooling from 80° C. to 85° C. down to 25° C. to 30° C. In some preferred embodiments, potassium sorbate is added to the water solution of PPG and at least one of methyl paraben and propyl paraben after or upon cooling to 25° C. to 30° C. More preferably, both methyl paraben and propyl paraben are added to the water and PPG solution at 80° C. to 85° C., and potassium sorbate is added after or upon cooling (with removal of heat, and without applying any external source) to 25° C. to 30° C. with stirring.

With continued reference to FIG. 1D, once the water solution with PPG and preservative(s) is at a temperature of 25° C. to 30° C., and optionally potassium sorbate added, an anti-foaming agent is added to the solution. Preferably, the anti-foaming agent is simethicone. In order to effectively mix the simethicone into the solution, 50% to 75% of the total final concentration of simethicone is added to the solution. More typically, 60% to 70% of the final concentration of simethicone is added to the solution, and preferably 67% of the final concentration of simethicone is added. For uniform dispersion of the simethicone, the solution is homogenized at 4,500 to 5,500 RPM for 30 to 50 minutes. Preferably, the solution is homogenized at 5,000 RPM for 45 minutes. In exemplary embodiments, simethicone is present in the stabilized suspension at a final concentration of between about 5 mg/mL to about 9 mg/mL. More preferably, simethicone is present at a final concentration between about 8 mg/mL to about 9 mg/mL.

With continued reference to FIG. 1D, after the simethicone is dispersed in the solution, microcrystalline cellulose (MCC) and a sweetening agent (e.g., sucralose, sucrose, glycerin, stevia, and/or sorbitol) are added with stirring either simultaneously or sequentially (e.g., one immediately after the other). Typically, the stirring is at 1,500 to 2,500 RPM for 15 to 25 minutes. In addition to or alternative to the stirring, the MCC and sweetening agent are homogenized in the solution at 6,000 to 7,000 RPM for about 40 to 50 minutes. Preferably, the homogenization occurs at 6,500 RPM for about 45 minutes. More preferably, the homogenization is carried out in addition to the stirring to thoroughly disperse the MCC. Most preferably, the sweetening agent is sucralose which at effective amounts is readily soluble and does not require additional time for dispersion. Typically, the MCC is present in the stabilized suspension at a final concentration of between about 10 to 20 mg/mL. More typically, the MCC is present in the stabilized suspension at a concentration of 20 mg/mL.

With continued reference to FIG. 1D, an anti-caking agent is added with stirring to the aqueous solution of PPG, preservative(s), simethicone, MCC, and a sweetening agent. The anti-caking agent is preferably hydroxyethylcellulose (HEC). The addition of an anti-caking agent like HEC increases the viscosity of the solution, and while both stirring and homogenization can effectively dissolve the HEC completely, homogenization may result in the formation of bubbles which is not desired. Typically, stirring is carried out at 1,500 to 2,500 RPM for 90 minutes (1.5 hours) to 150 minutes (2.5 hours). More typically, stirring is carried out at 2,000 RPM for 120 minutes (2 hours). Alternatively, while homogenization could cause the formation of bubbles, the addition of the remaining amount of simethicone added in Step II of Process B, will remove the bubbles.

With continued reference to FIG. 1D, a viscosity increasing agent is added with stirring to the aqueous solution of PPG, preservative(s) (e.g., methyl paraben, propyl paraben, and/or potassium sorbate), simethicone, MCC, the sweetening agent (e.g., sucralose), and the anti-caking agent (e.g., HEC). Preferably, the viscosity increasing agent is xanthum gum. The addition and dissolution of the viscosity increasing agent like xanthum gum is carried out with stirring. Typically, effective stirring for dissolution of the viscosity increasing agent (e.g., xanthum gum) is at 1,500 to 2,500 RPM for 40-80 minutes. More typically, effective stirring for dissolution of the viscosity increasing agent (e.g., xanthum gum) occurs at 2,000 RPM for 60 minutes (1 hour).

With continued reference to FIG. 1D, in the last step of Step I, glycerin is added with stirring to the aqueous solution of PPG, preservative(s) (e.g., methyl paraben and propyl paraben), simethicone, MCC, the sweetening agent (e.g., sucralose), the anti-caking agent (e.g., HEC), and the viscosity increasing agent (e.g., xanthum gum). Glycerin in this solution is a sweetener, a viscosity increasing agent, and an antimicrobial agent. By increasing the viscosity, glycerin reduces the sedimentation rate of the final suspension. The addition and dissolution of glycerin is carried out with stirring. Typically, effective stirring for dissolution of glycerin is at 1,500 to 2,500 RPM for 20-40 minutes. More typically, effective stirring for dissolution of glycerin occurs at 2,000 RPM for 30 minutes.

With reference to FIG. 1E, (Step II of Process B), a method for making a stabilized chlorthalidone suspension also includes preparing a second solution mixture starting with a volume of water (e.g., a second volume of water distinct and separate from the volume of water in Step I). This second volume of water is preferably between about 10% to 30% of the total volume of the final suspension. More preferably, the second volume of water is 20% of the total volume of the final suspension (e.g., the total batch size). To this volume of water, the remaining volume of simethicone is added relative to the amount added in Step I. Accordingly, if 50% to 75% of the total final concentration of simethicone is added in Step I, then a corresponding 25% to 50% is added to the second volume of water. More typically, 30% to 40% of the final concentration of simethicone is added to the second volume of water, and preferably 33% of the final concentration of simethicone is added to the second volume of water if 67% of the final concentration was added in Step I. Simethicone is used as an anti-foaming agent to prevent foam formation upon addition of a solubilizing and/or a wetting agent (e.g., Poloxamer 188). The simethicone is mixed into the second volume of water by homogenization. Typically, homogenization occurs at or between 4,500 to 5,500 RPM for 40 to 50 minutes. More typically, homogenization of the simethicone occurs at 5,000 RPM for 45 minutes.

With continued reference to FIG. 1E, a solubilizing and/or a wetting agent is added to the second water mixture and simethicone. Preferably, the solubilizing and/or a wetting agent is a wetting agent such as poloxamer 188. Typically, poloxamer 188 is dispersed into the second water mixture with simethicone by stirring at 1,800 to 2,200 RPM for 20 to 40 minutes. More typically, poloxamer 188 is dispersed into the second water mixture with simethicone by stirring at 2,000 RPM for 30 minutes.

With continued reference to FIG. 1E, chlorthalidone is added to the second water mixture of simethicone and a solubilizing and/or a wetting agent. Preferably, chlorthalidone is added at 5 mg/mL final concentration for the final volume/batch size. The chlorthalidone is added with stirring at 1,800 to 2,200 RPM for 20 to 30 minutes followed by homogenization at 6,000 to 7,000 RPM for 40 to 50 minutes. More preferably, chlorthalidone is added at 5 mg/mL final concentration with stirring at 2,000 RPM for 25 minutes followed by homogenization at 6,500 RPM for 45 minutes.

With reference to FIG. 1F, the solutions mixtures from Step I and Step II are combined and mixed. Typically, the colloidal solution of Step I is added to the solution of Step II. The combined solutions are mixed with stirring at 1,800 to 2,200 RPM for 20 to 40 minutes. Preferably the Step I and Step II solutions are mixed with stirring at 2,000 RPM for 30 minutes.

With reference to FIG. 1F, a buffering agent is added to the combined solutions, which upon mixing forms a stabilized chlorthalidone suspension (without added flavoring or color). Preferably, the buffering agent is citric acid anhydrous added at or between about 0.02 to 0.05 mg/mL. Preferably, citric acid anhydrous is added at 0.034 mg/mL. Subsequently, (e.g., one immediately added after the other) or simultaneously, a flavor, a flavoring agent, a coloring agent, and/or a dye, is added to the water solution, and is mixed with stirring for at 1,800 to 2,200 RPM for 90 minutes (1.5 hours) to 150 minutes (2.5 hours). Preferably, the stirring is at 2,000 RPM for 120 minutes (2 hours).

With continued reference to FIG. 1F, with the buffering agent (e.g., citric acid anhydrous) with or without a flavor, a flavoring agent, a coloring agent, and/or a dye dispersed into solution, the solution may be sampled and tested for quality control. For quality control testing, the chlorthalidone suspension may be tested for the concentration of one or more components. Typically, the chlorthalidone suspension is tested to confirm that a first concentration of the chlorthalidone in a first volume of the composition differs from a second concentration in a second volume of the composition by no more than 5%, as described in more detail herein. In other words, the chlorthalidone suspension is at least 95% homogenous with respect to the concentration of chlorthalidone found throughout the dispersion. Preferably, the chlorthalidone suspension is at least 95% homogenous with respect to all components throughout the suspension.

With continued reference to FIG. 1F, with the quality control sample or samples confirmed, the solution is then stirred at 1,500 to 2,500 RPM for 2 to 15 hours. Preferably, the verified solution is stirred at 2,000 RPM for 8 to 12 hours.

With reference to FIG. 2 and FIGS. 3A-3K, exemplary results show comparable data of various concentrations and the effects of the presently disclosed chlorthalidone dispersion with and without poloxamer and with and without hydroxyethylcellulose. Additionally, these results also show data for the chlorthalidone dispersion with and without simethicone, sucrose, silicon dioxide, and sorbitol, as well as flavors and colors as indicated (FIGS. 3A-3K).

Examples

With reference to Table 1A below, three exemplary chlorthalidone suspension formulations (Formulation 1, Formulation 2, and Formulation 3), were prepared following Process A as disclosed herein. Exemplary excipients including their function and IIG limit are indicated along with corresponding concentrations for each. As indicated, the amount of silicon dioxide varies for each of the formulations.

TABLE 1A

Formulation Composition (Process A)

| Active and Excipient Details | IIG Limit (mg/mL) | Function | Formulation-1 (mg/mL) | Formulation-2 (mg/mL) | Formulation-3 (mg/mL) |
|---|---|---|---|---|---|
| Chlorthalidone | API | Active | 10 | 10 | 10 |
| Water for Injection/ Deionized Water | Q.S. to mL | Vehicle | Q.S. to mL | Q.S. to mL | Q.S. to mL |
| Methyl Paraben | 200 | Antimicrobial Preservative | 1 | 1 | 1 |
| Propyl Paraben | 40 | Antimicrobial Preservative | 0.2 | 0.2 | 0.2 |
| Poloxamer 188 | 20 | Emulsifying/Wetting Agent | 10 | 10 | 10 |
| Simethicone (Density: 0.971) | 9 | Antifoaming Agent | 0.009 mL | 0.009 mL | 0.009 mL |
| Microcrystalline Cellulose (Avicel pH-101) | 20 | Suspending Agent | 20 | 20 | 20 |
| Sucrose | 500, 802.87 | Sweetening Agent | 150 | 150 | 150 |
| Silicon Dioxide | 67.94 | Viscosity-Increasing Agent | 50 | 10 | 20 |
| Hydroxyethyl cellulose | 0.25, 30 | Viscosity-Increasing Agent, Anticaking Agents | 2 | 2 | 2 |
| Sorbitol F Solution 70% in Water (Density: 1.46) | 975 | Sweetening Agent | 0.2 mL | 0.2 mL | 0.2 mL |
| Polyethylene Glycol 400 (Density: 1.13) | 50 | Viscosity-Increasing Agent, Antioxidant Agent | 0.044 mL | 0.044 mL | 0.044 mL |
| Strawberry Flavor ART WS (Density: 1.03) | 0.7 or 0.0006 mL, 1 or 0.001 mL | Flavor | 0.001 mL | 0.001 mL | 0.001 mL |
| FD & C Yellow #5/Tartrazine AL 15%-17% | 1* | Color | 0.5 | 0.5 | 0.5 |

*Maximum usage is not known.

With reference to Table 1B, the Formulations 1, 2, and 3 of Table 1A prepared by Process A are compared to the components for a stabilized chlorthalidone suspension prepared by Process B as disclosed herein and set forth in FIGS. 1D, 1E, and 1F.

TABLE 1B

Formulation Composition Comparison of Process A with Process B
Process A

| Active and Excipient Details | IIG Limit (mg/mL) | Function | Formulation-1 (mg/mL) | Formulation-2 (mg/mL) | Formulation-3 (mg/mL) |
|---|---|---|---|---|---|
| Chlorthalidone | API | Active | 10 | 10 | 10 |
| Water for Injection/ Deionized Water | Q.S. to mL | Vehicle | Q.S. to mL | Q.S. to mL | Q.S. to mL |
| Methyl Paraben | 200 | Antimicrobial Preservative | 1 | 1 | 1 |
| Propyl Paraben | 40 | Antimicrobial Preservative | 0.2 | 0.2 | 0.2 |
| Poloxamer 188 | 20 | Wetting agent | 10 | 10 | 10 |
| Simethicone (Density: 0.971) | 9 | Antifoaming Agent | 0.009 mL | 0.009 mL | 0.009 mL |
| Microcrystalline Cellulose (Avicel pH-101) | 20 | Suspending agent | 20 | 20 | 20 |
| Sucrose | 500, 802.87 | Sweetening Agent | 150 | 150 | 150 |
| Silicon Dioxide | 67.94 | Viscosity-Increasing Agent | 50 | 10 | 20 |
| Hydroxyethyl cellulose | 0.25, 30 | Viscosity-Increasing Agent, Anticaking Agents | 2 | 2 | 2 |
| Sorbitol F Solution 70% in Water (Denstiy: 1.46 | 975 | Sweetening Agent | 0.2 mL | 0.2 mL | 0.2 mL |

TABLE 1B-continued

Formulation Composition Comparison of Process A with Process B
Process A

| Active and Excipient Details | IIG Limit (mg/mL) | Function | Formulation-1 (mg/mL) | Formulation-2 (mg/mL) | Formulation-3 (mg/mL) |
|---|---|---|---|---|---|
| Polyethyleme Glycol 400 (Density: 1.13) | 50 | Viscosity-Increasing Agent Antioxidant Agent | 0.044 mL | 0.044 mL | 0.044 mL |
| Strawberry Flavor ART WS (Density: 1.03) | 0.7 or 0.0006 mL, 1 or 0.001 mL | Flavor | 0.001 mL | 0.001 mL | 0.001 mL |
| FD & C Yellow #5/ Tartrazine AL 15%-17% | 1* | Color | 0.5 | 0.5 | 0.5 |

With reference to Table 2, each of Formulation 1, 2, and 3 was prepared as a 500 ml (Formulation 1) or 1,000 ml batch size (Formulation 2 and 3) following the methods disclosed herein and set forth in FIGS. 1A, 1B, and 1C, with 50, 10, or 20 mg/mL silicon dioxide as indicated, with observations noted (Remarks).

TABLE 2

Batch Details

Formulation trials of Chlorthalidone Oral Suspension 10 mg/vial

| Active and Excipient Details | Formulation 1 B.No. # NCH1972 Batch Size: 500 mL | | Formulation 2 B.No. # NCH1979 Batch Size: 1000 mL | | Formulation 3 B.No. # NCH1984 Batch Size: 1000 mL | | Remarks |
|---|---|---|---|---|---|---|---|
| | mg/mL | Batch Qty. | mg/mL | Batch Qty. | mg/mL | Batch Qty. | |
| Chlorthalidone | 10 | 5 g or 5000 mg | 10 | 10 g or 10000 mg | 10 | 10 g or 10000 mg | In Formulation 1, more lumps are observed after addition of Silicon dioxide. So two more batches manufactured using less quantity of Silicon dioxide. Formulation 3 found suitable as a suspension compare to Formulation 2 which look like a low viscous and low dense suspension. |
| Water for Injection/Deionized Water | Q.S. to mL | Q.S. to 500 mL | Q.S. to mL | Q.S. to 1000 mL | Q.S. to mL | Q.S. to 1000 mL | |
| Methyl Paraben | 1 | 500 mg | 1 | 1000 mg | 1 | 1000 mg | |
| Propyl Paraben | 0.2 | 100 mg | 0.2 | 200 mg | 0.2 | 200 mg | |
| Polaxamer 188 | 10 | 5000 mg or 5 g | 10 | 10000 mg or 10 g | 10 | 10000 mg or 10 g | |
| Simethicone (Density: 0.971) | 0.009 mL | 4.5 mL | 0.009 mL | 9 mL | 0.009 mL | 9 mL | |
| Microcrystalline Cellulose (Avicel pH-101) | 20 | 10000 mg or 10 g | 20 | 20000 mg or 20 g | 20 | 20000 mg or 20 g | |
| Sucrose | 150 | 75000 mg or 75 g | 150 | 150000 mg or 150 g | 150 | 150000 mg or 150 g | |
| Silicon Dioxide | 50 | 25000 mg or 25 g | 10 | 10000 mg or 10 g | 20 | 20000 mg or 20 g | |
| Hydroxyethyl cellulose | 2 | 1000 mg or 1 g | 2 | 2000 mg or 2 g | 2 | 2000 mg or 2 g | |
| Sorbitol F Solution 70% in Water (Density: 1.46) | 0.2 mL | 100 mL | 0.2 mL | 200 mL | 0.2 mL | 200 mL | |
| Polyethylene Glycol 400 (Density: 1.13) | 0.044 mL | 22 mL | 0.044 mL | 44 mL | 0.044 mL | 44 mL | |
| Strawberry Flavor ART WS (Density: 1.03) | 0.001 mL | 0.5 mL | 0.001 mL | 1 mL | 0.001 mL | 1 mL | |
| FD & C Yellow #5/Tartrazine AL 15%-17% | 0.5 | 250 mg or 0.25 g | 0.5 | 500 mg or 0.5 g | 0.5 | 500 mg or 0.5 g | |

With reference to Table 3, dissolution of chlorthalidone in a suspension pursuant to Formulation 1 (NCH1972) and Formulation 2 (NCH1979) was compared to the dissolution of 50 mg tablets of chlorthalidone as indicated. Notably, with reference to FIG. 2, the dissolution of Formulation 1 and Formulation 2 occurred within 5 minutes and was maintained for at least 1 hour (60 minutes). Comparatively, the 50 mg tablets did not disperse or dissolve as quickly, and not as much of the chlorthalidone went into solution after 1 hour.

TABLE 3

Comparative Dissolution Profile Tablet Vs Suspension

| Product Name: | Chlorthalidone Oral Suspension 10 mg/mL | | Chlorthalidone Oral Suspension 5 mg/mL | Chlorthalidone Tablets 50 mg |
|---|---|---|---|---|
| Batch No.: | NCH1972 | NCH1979 | NCH19122 | CHBUO6 |
| Condition: | Initial | Initial | Initial | Initial |

| Dissolution Condition: | | | | |
|---|---|---|---|---|
| Apparatus | USP Type II | USP Type II | USP Type II | USP Type II |
| Volume | 900 mL | 900 mL | 900 mL | 900 mL |
| RPM | 75 RPM | 75 RPM | 75 RPM | 75 RPM |
| Temperature | 37.0 ± 0.5° C. | 37.0 ± 0.5° C. | 37.0 ± 0.5° C. | 37.0 ± 0.5° C. |
| Sampling point in minute | 5, 15, 30, 45, 60 | 5, 15, 30, 45, 60 | 5, 15, 30, 45, 60 | 5, 15, 30, 45, 60 |
| Time in minute | % of dissolution | % of dissolution | % of dissolution | % of dissolution |
| 0 | 0 | 0 | 0 | 0 |
| 5 | 106 | 109 | 99 | 85 |
| 15 | 106 | 108 | 94 | 89 |
| 30 | 106 | 107 | 96 | 93 |
| 45 | 106 | 106 | 92 | 94 |
| 60 | 106 | 105 | 92 | 95 |

| Product Name: | Chlorthalidone Tablets 50 mg | Chlorthalidone Tablets 50 mg | Chlorthalidone Tablets 50 mg |
|---|---|---|---|
| Batch No.: | CHBUO3 (Bio Batch) | 3074250_50 mg_Mylan | 3030080_25 mg_Mylan |
| Condition: | Initial | Initial | Initial |

| Dissolution Condition: | | | |
|---|---|---|---|
| Apparatus | USP Type II | USP Type II | USP Type II |
| Volume | 900 mL | 900 mL | 900 mL |
| RPM | 75 RPM | 75 RPM | 75 RPM |
| Temperature | 37.0 ± 0.5° C. | 37.0 ± 0.5° C. | 37.0 ± 0.5° C. |
| Sampling point in minute | 5, 15, 30, 45, 60 | 5, 15, 30, 45, 60 | 5, 15, 30, 45, 60 |
| Time in minute | % of dissolution | % of dissolution | % of dissolution |
| 0 | 0 | 0 | 0 |
| 5 | 57 | 44 | 53 |
| 15 | 76 | 66 | 80 |
| 30 | 87 | 78 | 93 |
| 45 | 92 | 84 | 97 |
| 60 | 95 | 88 | 99 |

With reference to Table 4, each of Formulation 1, 2 and 3 was analyzed for settling. In other words, the concentration of each of chlorthalidone, methyl paraben, and propyl paraben was analyzed throughout the suspension in order to determine the degree of dispersion of each in the suspension. Accordingly, for each of three suspensions, two samples were taken from the bottom, the middle and the top of the suspension and the concentration of chlorthalidone, methylparaben, and propylparaben were quantified for each sample. As indicated, the concentration of chlorthalidone in each of the samples varied (i.e., differed) by no more than 1%.

TABLE 4

Analytical Results

| | | Batch No.: NCH1972 | | | Batch No.: NCH1979 | | | Batch No.: NCH1984 | | |
|---|---|---|---|---|---|---|---|---|---|---|
| Analytical Data | Samples | Chlortha-lidone | Methyl Paraben | Propyl Paraben | Chlortha-lidone | Methyl Paraben | Propyl Paraben | Chlortha-lidone | Methyl Paraben | Propyl Paraben |
| Assay | Bottom-1 | 106.3 | 101.7 | 99.8 | 104.5 | 102.3 | 98.7 | 99.9 | 101.2 | 98.2 |
| | Bottom-2 | 106.9 | 102.2 | 100.7 | 104.1 | 102.3 | 99.4 | 100.2 | 101.4 | 98.3 |
| | Middle-1 | 107.0 | 102.1 | 100.2 | 102.1 | 100.1 | 97.2 | 100.0 | 101.3 | 98.0 |
| | Middle-2 | 106.4 | 102.0 | 99.9 | 101.9 | 100.0 | 97.0 | 100.3. | 101.5 | 98.4 |
| | Top-1 | 106.5 | 101.9 | 99.6 | 101.8 | 100.2 | 97.2 | 99.4 | 100.7 | 97.5 |
| | Top-2 | 106.5 | 101.7 | 99.6 | 101.9 | 99.9 | 97.2 | 99.7 | 101.0 | 97.8 |
| Observation | | Batch QS made with volume. | | | NA | | | Batch QS made with weight. | | |
| pH | | 5.21 | | | 5.34 | | | 5.54 | | |
| Density | | 1.1764 g/cm3 | | | 1.12941 g/cm3 | | | 1.17897 g/cm3 | | |
| Viscocity | | 290 cp | | | 260 cp | | | 250 cp | | |
| Deliverable volume | | NA | | | NA | | | Complies as per USP <698> for multi unit container for not less than 100% LV | | |

TABLE 4-continued

Analytical Results

| | | Batch No.: NCH1972 | | | Batch No.: NCH1979 | | | Batch No.: NCH1984 | | |
|---|---|---|---|---|---|---|---|---|---|---|
| Analytical Data | Samples | Chlortha-lidone | Methyl Paraben | Propyl Paraben | Chlortha-lidone | Methyl Paraben | Propyl Paraben | Chlortha-lidone | Methyl Paraben | Propyl Paraben |
| Dissolution (75 RPM. Water, 30 minutes) | Sample-1 | 106 | Not Applicable | | 107 | Not Applicable | | 102 | Not Applicable | |
| | Sample-2 | 106 | | | 108 | | | 106 | | |
| | Sample-3 | 106 | | | 107 | | | 107 | | |
| | Sample-4 | 106 | | | 107 | | | 108 | | |
| | Sample-5 | 105 | | | 107 | | | 105 | | |
| | Sample-6 | 105 | | | 106 | | | 103 | | |
| | Mean | 106 | | | 107 | | | 105 | | |

With reference to Table 5, each of Formulations 1, 2, and 3 (NCH1972, NCH1979, NCH1984) were analyzed for impurities.

TABLE 5

Impurity Data

| Impurity Name | Limit | B.No. # IF1500690A (Euticals API) |
|---|---|---|
| Imp-B/Chlorthalidone Related Compound-A | NMT 0.7% | 0.28 |
| Imp-J | NMT 0.3% | 0.01 |
| Imp-G | NMT 0.2% | 0.10 |
| Any unspecified impurity | NMT 0.1% | 0.05 |
| Total Impurity | NMT 1.0% | 0.48 |

| | | B.No. # NCH1972 | | B.No. # NCH1979 | B.No. # NCH1984 |
|---|---|---|---|---|---|
| Impurity Name | Limit | Sample-1 | Sample-2 | Sample-1 | Sample-1 |
| Imp-A | NMT 0.7% | 0.45 | 0.45 | 0.41 | 0.39 |
| Imp-J | NMT 0.2% | 0.02 | 0.02 | 0.01 | 0.00 |
| Imp-G | NMT 0.2% | 0.11 | 0.12 | 0.11 | 0.11 |
| CPSP | NMT 0.10% | ND | ND | ND | ND |
| Any Individual | NMT 0.20% | 0.05 | 0.05 | 0.01 | 0.01 |
| Total Imp [Excluding Imp-A] | NMT 0.80% | 0.18 | 0.19 | 0.13 | 0.12 |

With reference to FIGS. 4A-4F, 5A-5F, 6A-6F, and 7A-7F, stability and settling analysis was carried out at 25° C. and 40° C. as indicated for each of the exemplary chlorthalidone batches of NCH1972, NCH1979, NCH1984, and NC19122.

With reference to Table 6, the batch No. CHLL1009 was prepared with the following composition:

TABLE 6

Composition Batch No. CHLL1009

| Sr. No. | Ingredients | Specification | Quantity (mg/mL) |
|---|---|---|---|
| 1 | Chlorthalidone | USP | 5.00 |
| 2 | Methyl paraben | NF | 1.80 |
| 3 | Propyl paraben | NF | 0.20 |
| 4 | Sodium Dihydrogen Phosphate Dihyrate | USP | 1.37 |
| 5 | Disodium Hydrogen Phosphate Dihyrate | USP | 0.22 |
| 6 | Sucralose Powder | NF | 0.50 |
| 7 | 30% Simethicone Emulsion | USP | 5.00 |
| 8 | Glycerin | USP | 100.00 |
| 9 | Xanthan Gum | NF | 5.00 |
| 10 | Purified Water | USP | Q.S. to 1.00 mL |

With reference to Table 7 below, the composition of Table 6 was prepared using the following bulk manufacturing steps:

TABLE 7

| Bulk manufacturing steps | | |
|---|---|---|
| 1. | Bulk Manufacturing | |
| 1.1 | Tare weight of SS manufacturing vessel (S1) (kg): Add 80 L Purified water (80% of total batch size) in SS manufacturing vessel (S1). | |
| 1.2 | Increase the temperature of the solution of Step 1.1 to 75-80° C. and maintain it. | |
| | Stirring speed | 200-500 RPM |
| | Temperature | 75-80° C. |
| 1.3 | Add dispensed quantity of Methyl paraben in SS manufacturing vessel (S1) Step 1.2 and stir well until clear solution is obtained. | |
| | Stirring speed | 200-500 RPM |
| | Mixing Time | 10 min |
| | Temperature | 75-80° C. |
| 1.4 | Add dispensed quantity of Propyl paraben in SS manufacturing vessel (S1) Step 1.3 and stir well until clear solution is obtained. | |
| | Stirring speed | 200-500 RPM |
| | Mixing Time | 10 min |
| | Temperature | 75-80° C. |
| 1.5 | Cool the solution of Step 1.4, to 20-30° C. under stirring. Add purified water to adjust water loss observed during Step 1.2 to Step 1.4. | |
| | Stirring speed | 200-500 RPM |
| | Mixing Time | 10 min |
| 1.6 | Add dispensed quantity of Sodium Dihydrogen Phosphate Dihydrate in SS manufacturing vessel (S1) Step 1.5 and stir well. | |
| | Stirring speed | 200-500 RPM |
| | Mixing Time | 10 min |
| 1.7 | Add dispensed quantity of Disodium Hydrogen Phosphate Dihydrate in SS manufacturing vessel (S1) Step 1.6 and stir well. | |
| | Stirring speed | 200-500 RPM |
| | Mixing Time | 10 min |
| 1.8 | Add dispensed quantity of sucralose in SS manufacturing vessel (S1) Step 1.7 and stir well. | |
| | Stirring speed | 200-500 RPM |
| | Mixing Time | 10 min |
| 1.9 | Add dispensed quantity of 30% Simethicone Emulsion in SS manufacturing vessel (S1) Step 1.8 and stir well. | |
| | Stirring speed | 200-500 RPM |
| | Mixing Time | 10 min |
| 1.10 | Tare weight of SS manufacturing vessel (S2) (kg): Add dispensed quantity of Glycerin in SS manufacturing vessel (S2). | |
| 1.11 | Add dispensed quantity of Chlorthalidone to SS Manufacturing vessel (S2) Step 1.10 and stir well. | |
| | Stirring speed | 300-500 RPM |
| | Mixing Time | 5 min |
| 1.12 | Add dispensed quantity of Xanthan gum to SS Manufacturing vessel (S2) Step 1.11 and stir well. | |
| | Stirring speed | 300-500 RPM |
| | Mixing Time | 5 min |
| 1.13 | Add content of SS Manufacturing vessel (S2) Step 1.12 to SS Manufacturing vessel (S1) Step 1.9 and stir well. | |
| | Stirring speed | 300-500 RPM |
| | Mixing Time | 60 min |
| 1.14 | Add remaining quantity of Purified water in SS manufacturing vessel (S1) to make up the volume and mix until uniform suspension is obtained. | |
| | Stirring speed | 300-500 RPM |
| | Mixing Time | NLT 15 min |
| 1.15 | Connect the SS manufacturing vessel (S1) Step 1.14 to inline homogenizer to homogenize the suspension. | |
| | Homogenization speed | 5000 ± 200 RPM |
| | Homogenization time | 30 min |

With reference to Table 8 below, stability data for CHLL1009 batch is as follows:

TABLE 8

| Stability data | | | | |
|---|---|---|---|---|
| Sr | | Limit | RS - Mylan | | |
| 1 | RLD/ Development | — | 50 mg Tablet | Development | Development |
| 2 | Batch No. | — | 2008545 | CHLL1009 | CHLL1009 |
| 4 | T0/Stability Time Point | — | T0 | T0 | 40° C./25% - 1 Month |

TABLE 8-continued

| Sr | | | | | |
|---|---|---|---|---|---|
| 5 | Pack | — | HDPE Bottle | 330 mL White PET | 330 mL White PET |
| 6 | API source Lot No. API PSD | — | — | AMRI IF1902346A D(100) 60 μm | AMRI IF1902346A D(100) 60 μm |
| 7 | Appearance | — | Light green, round, scored tablets debossed with M to the left of the score and 75 to the right of the score on one side of the tablet and blank on the other side. | Off white suspension | Off white suspension |
| 8 | Viscosity | To be recorded | NA | 157.5 cps | 155.5 cps |
| 9 | Assay of Chlorthalidone | 90 to 110% | 99.6% | 101.4% | 101.5% |
| 10.1 | Content of Methyl | 80 to 110% | NA | 97.1% | 97.0% |
| 10.2 | Content of Propyl paraben | 80 to 110% | NA | 97.5% | 97.6% |
| 11 | pH | To be recorded | — | 5.9 | 5.8 |
| 12 | Specific Gravity (gm/mL) | To be recorded | NA | 1.01 | 1.01 |
| 13 | Zeta Potential (mV) | To be recorded | NA | −22.6 | −27.9 |
| 14 | Particle Size Distribution | | | | |
| | D(10) | To be recorded | NA | 2.0 μm | 2.1 μm |
| | D(50) | To be recorded | NA | 6.4 μm | 7.0 μm |
| | D(90) | To be recorded | NA | 19.5 μm | 20.6 μm |
| 15 | Related Substances | | | | |
| 15.1 | Chlorthalidone Related | NMT 1.0% | 0.29% | 0.39% | 0.39% |
| 15.2 | Impurity-J | NMT 0.2% | ND | ND | ND |
| 15.3 | Impurity-G | NMT 0.2% | 0.17% | 0.13% | 0.13% |
| 15.4 | Impurity-E (CPSP) | NMT 0.1% | ND | ND | ND |
| 15.5 | Single Max unspecified | NMT 0.2% | 0.05% | 0.08% | 0.07% |
| 15.6 | Total impurities | NMT 1.2% | 0.72% | 0.79% | 0.81% |

| Sr | | | | | |
|---|---|---|---|---|---|
| 1 | RLD/ Development | Development | Development | Development | Development |
| 2 | Batch No. | CHLL1009 | CHLL1009 | CHLL1009 | CHLL1009 |
| 4 | T0/Stability Time Point | 40° C./25% - 3 Months | 40° C./25% - 6 Months | 25° C./40% - 3 Months | 25° C./40% - 6 Months |
| 5 | Pack | 330 mL White PET | 330 mL White PET | 330 mL White PET | 330 mL White PET |
| 6 | API source Lot No. API PSD | AMRI IF1902346A D(100) 60 μm | AMRI IF1902346A D(100) 60 μm | AMRI IF1902346A D(100) 60 μm | AMRI IF1902346A D(100) 60 μm |
| 7 | Appearance | Off white suspension | Off white suspension | Off white suspension | Off white suspension |
| 8 | Viscosity | 151.5 cps | 141.5 cps | 155.5 cps | 149.0 cps |
| 9 | Assay of Chlorthalidone | 101.7% | 102.6% | 101.5% | 101.3% |
| 10.1 | Content of Methyl | 96.7% | 97.0% | 97.5% | 97.2% |
| 10.2 | Content of Propyl paraben | 97.0% | 98.9% | 97.7% | 99.4% |
| 11 | pH | 5.5 | 5.1 | 5.8 | 5.7 |
| 12 | Specific Gravity (gm/mL) | 1.01 | 1.02 | 1.01 | 1.01 |
| 13 | Zeta Potential (mV) | −28.4 | −22.2 | −24.8 | −19.8 |
| 14 | Particle Size Distribution | | | | |
| | D(10) | 2.0 μm | 2.0 μm | 2.0 μm | 2.0 μm |
| | D(50) | 7.0 μm | 6.3 μm | 6.8 μm | 6.4 μm |
| | D(90) | 23.2 μm | 17.5 μm | 22.1 μm | 20.0 μm |
| 15 | Related Substances | | | | |
| 15.1 | Chlorthalidone Related | 0.46% | 0.44% | 0.41% | 0.38% |

TABLE 8-continued

| | | | | | |
|---|---|---|---|---|---|
| 15.2 | Impurity-J | ND | ND | ND | ND |
| 153 | Impurity-G | 0.14% | 0.13% | 0.14% | 0.13% |
| 15.4 | Impurity-E (CPSP) | ND | ND | ND | ND |
| 15.5 | Single Max unspecified | 0.10% | 0.19% | 0.07% | 0.09% |
| 15.6 | Total impurities | 1.06% | 1.18% | 0.88% | 0.82% |

Finally, with regard to Table 9 below, dissolution data in various media is presented below:

TABLE 9

Multimedia dissolution data

Chlorthalidone Suspension 5 mg/mL - Multimedia Dissolution

| Batch No. | API Lot No/ Particle Size | Media | | RPM 75 RPM | 5 min | 10 min | 15 min | 30 min | 45 min | 60 min | 75 min | F2 with RS - Mylan | F2 with Nivagen Bio Batch |
|---|---|---|---|---|---|---|---|---|---|---|---|---|---|
| CHBU03 Bio Batch | Nivagen Bio Batch | OGD (Purified Water) | Drug Release | | 57 | 69 | 76 | 87 | 92 | 95 | — | 50 | NA |
| | | 0.1 N HCL | Drug Release | | 51 | 66 | 76 | 91 | 97 | 102 | 104 | 48 | NA |
| | | pH 4.5 Acetate Buffer | Drug Release | | 52 | 65 | 74 | 86 | 91 | 93 | 96 | 56 | NA |
| | | pH 6.8 Phosphate Buffer | Drug Release | | 52 | 65 | 72 | 83 | 88 | 91 | 93 | 47 | NA |
| 2009364 RS 50 mg | Mylan- RS | OGD (Purified Water) | Drug Release | | 40.9 | 55.7 | 64.5 | 78.1 | 84.7 | 88.6 | 91.1 | NA | NA |
| | | 0.1 N HCL | Drug Release | | 32.2 | 48.3 | 57.9 | 73.1 | 80.4 | 84.8 | 87.7 | NA | NA |
| | | pH 4.5 Acetate Buffer | Drug Release | | 34.6 | 49.6 | 58.6 | 73.1 | 80.3 | 84.8 | 87.8 | NA | NA |
| | | pH 6.8 Phosphate Buffer | Drug Release | | 35.3 | 49.5 | 58.1 | 72.2 | 79.4 | 83.9 | 87.0 | NA | NA |
| CHLL1009 | AMRI 1F1902346A D100 = 60 μm (D90 =14 μm) | OGD (Purified Water) | Drug Release | | 78.8 | 91.3 | 95.4 | 97.5 | 97.6 | 97.5 | 97.6 | 29 | 36 |
| | | 0.1 N HCL | Drug Release | | 86.8 | 94.6 | 97.1 | 99.0 | 99.3 | 99.3 | 99.4 | 23 | 30 |
| | | pH 4.5 Acetate Buffer | Drug Release | | 78.9 | 87.6 | 94.2 | 98.9 | 98.8 | 98.8 | 100.8 | 27 | 34 |
| | | pH 6.8 Phosphate Buffer | Drug Release | | 55.1 | 69.5 | 74.9 | 90.1 | 94.9 | 97.6 | 101.3 | 38 | 64 |

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

Unless the context dictates the contrary, all ranges set forth herein should be interpreted as being inclusive of their endpoints and open-ended ranges should be interpreted to include only commercially practical values. Similarly, all lists of values should be considered as inclusive of intermediate values unless the context indicates the contrary.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value with a range is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A composition comprising a stabilized chlorthalidone suspension, the stabilized chlorthalidone suspension, comprising:
    chlorthalidone, wherein the chlorthalidone is undissolved in the suspension and wherein the undissolved chlorthalidone is present in the suspension at a concentration of between 1 to 20 mg/mL;
    a solubilizing or wetting agent;
    at least one suspending agent;
    at least one viscosity increasing agent or at least one anti-caking agent; and
    water;
    wherein the solubilizing or wetting agent, the at least one suspending agent, and the at least one viscosity increasing agent or at least one anti-caking agent are present in respective quantities to provide uniform dispersion of the undissolved chlorthalidone following initial stirring of the suspension so that a first chlorthalidone concentration in a first sample of the composition differs from a second sample in a second volume of the composition by no more than 5% after storage for at least 60 min without stirring.

2. The composition as in claim 1, wherein the first chlorthalidone concentration in the first sample of the composition differs from the second sample in the second volume of the composition by no more than 5% after storage for at least 24 hours without stirring.

3. The composition of claim 1, wherein the first sample concentration of the chlorthalidone in the first volume of the composition differs from the second sample concentration in the second volume of the composition of the same batch by no more than 2.5%.

4. The composition of claim 1, wherein the stabilized chlorthalidone suspension further comprises one or more selected from the group consisting of an anti-foaming agent, at least one antimicrobial, and at least one sweetening agent.

5. The composition of claim 1, wherein the chlorthalidone is present in the composition at a concentration of between about 5 to 15 mg/mL.

6. The composition of claim 5, wherein the chlorthalidone is present in the composition at a concentration of about 5 or 10 mg/mL.

7. The composition of claim 1, wherein the solubilizing or wetting agent is selected from the group consisting of propylene glycol (PPG), poloxamer 188, poloxamer 124, and poloxamer 237.

8. The composition of claim 7, wherein the solubilizing or wetting agent is poloxamer 188, which is present in the composition at a concentration of between about 5 to 20 mg/mL.

9. The composition of claim 1, wherein the suspending agent is a polysaccharide suspending agent and/or a synthetic suspending agent.

10. The composition of claim 9, wherein the polysaccharide suspending agent is one or more selected from microcrystalline cellulose (MCC), acacia gum, tragacanth gum, xanthan gums, starch, or alginates.

11. The composition of claim 10, wherein the MCC is present in the composition at a concentration of between about 10 to 20 mg/mL.

12. The composition of claim 1, wherein the at least one viscosity increasing agent or at least one anti-caking agent is selected from hydroxyethylcellulose, silicon dioxide, polyethylene glycol (PEG), xanthan gum, or glycerin.

13. The composition of claim 12, wherein the at least one viscosity increasing agent or the at least one anti-caking agent is present in the composition of between 0.1 to 5% by weight (wt %).

14. The composition of claim 4, wherein the anti-foaming agent is simethicone.

15. The composition of claim 4, wherein the at least one antimicrobial is methyl and propyl paraben.

16. A method for making a stabilized chlorthalidone suspension, comprising:
    forming a first mixture by
        adding a solubilizing or wetting agent to a first volume of water having a temperature of between about 25° C. to 30° C. with stirring;
        wherein the first volume of water is 50% of the stabilized chlorthalidone suspension;
        adding a suspending agent to the first volume of water with stirring and homogenizing; and
        adding at least one viscosity increasing agent or at least one anti-caking agent to the first volume of water with stirring and homogenizing;
    forming a second mixture by
        adding a sweetening agent to a second volume of water with stirring;
        adding a viscosity increasing agent to the second volume of water with stirring; and
        adding chlorthalidone at between about 5 to 20 mg/mL to the second volume of water with stirring and homogenizing; and
    forming the stabilized chlorthalidone suspension by
        adding the first mixture to the second mixture with stirring to form a third mixture;
        optionally adding a third volume of water to the third mixture to thereby render a final volume; and
        homogenizing the third mixture to form the stabilized chlorthalidone suspension.

17. The method of claim 16, wherein forming the first mixture further comprises:
    prior to adding the solubilizing or the wetting agent to the water, heating the water to about 80° C. to 85° C.;
    adding at least one antimicrobial preservative to the heated water with stirring; and
    ambiently cooling the water to about 25° C. to 30° C.

18. The method of claim 16, wherein forming the first mixture further comprises:

adding potassium sorbate; and adding an anti-foaming agent with stirring.

19. The method claim 16, wherein forming the first mixture further comprises:
adding in a sweetening agent with stirring and homogenizing, the sweetening agent is sucrose, sucralose, glycerin, stevia, and/or sorbitol.

20. The method of claim 16, wherein the at least one viscosity increasing agent or the at least one anti-caking agent selected from hydroxyethylcellulose and/or silicon dioxide.

* * * * *